(12) United States Patent
Bruggemann

(10) Patent No.: US 8,329,981 B2
(45) Date of Patent: *Dec. 11, 2012

(54) GENETICALLY MODIFIED NON-HUMAN MAMMALS AND CELLS

(75) Inventor: Marianne Bruggemann, Cambridge (GB)

(73) Assignee: Crescendo Biologics Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/081,035

(22) Filed: Apr. 6, 2011

(65) Prior Publication Data

US 2011/0277047 A1    Nov. 10, 2011

Related U.S. Application Data

(63) Continuation of application No. 10/547,066, filed as application No. PCT/GB2004/000768 on Feb. 26, 2004, now Pat. No. 7,932,431.

(30) Foreign Application Priority Data

Feb. 26, 2003   (GB) .................................. 0304374.2

(51) Int. Cl.
*A01K 67/033*   (2006.01)
*A01A 63/00*   (2006.01)

(52) U.S. Cl. ............. 800/18; 424/93.2; 800/13; 800/14; 800/21

(58) Field of Classification Search ........................ None
See application file for complete search history.

(56) References Cited

U.S. PATENT DOCUMENTS 7,932,431 B2 *   4/2011   Bruggemann .................. 800/18

* cited by examiner

*Primary Examiner* — Q. Janice Li
(74) *Attorney, Agent, or Firm* — Wolf, Greenfield & Sacks, P.C.

(57) ABSTRACT

A genetically modified mouse characterized in that it does not comprise a nucleic acid sequence which itself encodes any endogenous immunoglobulin heavy chain constant region locus polypeptide.

11 Claims, 26 Drawing Sheets

SEQUENCE LISTING

```
<160> NUMBER OF SEQ ID NOS: 23

<210> SEQ ID NO 1
<211> LENGTH: 64
<212> TYPE: DNA
<213> ORGANISM: Artificial Sequence
<220> FEATURE:
<223> OTHER INFORMATION: Forward primer BamHI - lox P - puro

<400> SEQUENCE: 1
tttggatcca taacttcgta taatgtatgc tatacgaagt tatcgacctc gaaattctac    60
cggg                                                                 64

<210> SEQ ID NO 2
<211> LENGTH: 28
<212> TYPE: DNA
<213> ORGANISM: Artificial Sequence
<220> FEATURE:
<223> OTHER INFORMATION: Reverse primer oligo BclI - puro

<400> SEQUENCE: 2
tttgatcagc tgatctcgtt cttcaggc                                       28

<210> SEQ ID NO 3
<211> LENGTH: 18
<212> TYPE: DNA
<213> ORGANISM: Artificial Sequence
<220> FEATURE:
<223> OTHER INFORMATION: Forward primer

<400> SEQUENCE: 3
aacctgacat gttcctcc                                                  18

<210> SEQ ID NO 4
<211> LENGTH: 18
<212> TYPE: DNA
<213> ORGANISM: Artificial Sequence
<220> FEATURE:
<223> OTHER INFORMATION: Reverse primer

<400> SEQUENCE: 4
gggattagct gagtgtgg                                                  18
```

```
<210> SEQ ID NO 5
<211> LENGTH: 27
<212> TYPE: DNA
<213> ORGANISM: Artificial Sequence
<220> FEATURE:
<223> OTHER INFORMATION: P1 V000818f pri MIgHK01F forward primer that
      binds to the mu region

<400> SEQUENCE: 5
agagccccct gtctgataag aatctgg                                           27

<210> SEQ ID NO 6
<211> LENGTH: 23
<212> TYPE: DNA
<213> ORGANISM: Artificial Sequence
<220> FEATURE:
<223> OTHER INFORMATION: P2 Purinomycinr pri MIgHK02R reverse primer
      that binds to the mu region

<400> SEQUENCE: 6
tggatgtgga atgtgtgcga ggc                                               23

<210> SEQ ID NO 7
<211> LENGTH: 23
<212> TYPE: DNA
<213> ORGANISM: Artificial Sequence
<220> FEATURE:
<223> OTHER INFORMATION: P3 Neomycinf pri MIgHK03F forward primer that
      binds to the 3' enhancer region

<400> SEQUENCE: 7
tgctttacgg tatcgccgct ccc                                               23

<210> SEQ ID NO 8
<211> LENGTH: 22
<212> TYPE: DNA
<213> ORGANISM: Artificial Sequence
<220> FEATURE:
<223> OTHER INFORMATION: P4 X96607r pri MIgHK04R reverse primer that
      binds to the 3' enhancer region

<400> SEQUENCE: 8
gagtccccat ccccaaggct gg                                                22

<210> SEQ ID NO 9
<211> LENGTH: 23
<212> TYPE: DNA
<213> ORGANISM: Artificial Sequence
<220> FEATURE:
<223> OTHER INFORMATION: Cre forward primer

<400> SEQUENCE: 9
ggacatgttc agggatcgcc agg                                               23

<210> SEQ ID NO 10
<211> LENGTH: 23
<212> TYPE: DNA
<213> ORGANISM: Artificial Sequence
<220> FEATURE:
<223> OTHER INFORMATION: Cre reverse primer

<400> SEQUENCE: 10
gatagctggc tggtggcaga tgg                                               23

<210> SEQ ID NO 11
<211> LENGTH: 28
<212> TYPE: DNA
```

```
<213> ORGANISM: Artificial Sequence
<220> FEATURE:
<223> OTHER INFORMATION: Gamma 2a primer

<400> SEQUENCE: 11
gtagctattt ctttccaccc agttcttc                                      28

<210> SEQ ID NO 12
<211> LENGTH: 28
<212> TYPE: DNA
<213> ORGANISM: Artificial Sequence
<220> FEATURE:
<223> OTHER INFORMATION: Gamma 2a a reverse primer

<400> SEQUENCE: 12
gtagctattt ctttccaccc agttcttc                                      28

<210> SEQ ID NO 13
<211> LENGTH: 28
<212> TYPE: DNA
<213> ORGANISM: Artificial Sequence
<220> FEATURE:
<223> OTHER INFORMATION: Gamma 2a b reverse primer

<400> SEQUENCE: 13
gaaaagactt cctctttccc aagtgctc                                      28

<210> SEQ ID NO 14
<211> LENGTH: 20
<212> TYPE: DNA
<213> ORGANISM: Artificial Sequence
<220> FEATURE:
<223> OTHER INFORMATION: DF forward primer

<400> SEQUENCE: 14
gcatgtctca aagcacaatg                                               20

<210> SEQ ID NO 15
<211> LENGTH: 20
<212> TYPE: DNA
<213> ORGANISM: Artificial Sequence
<220> FEATURE:
<223> OTHER INFORMATION: DQ52 reverse primer

<400> SEQUENCE: 15
accctggaca caggaaacac                                               20

<210> SEQ ID NO 16
<211> LENGTH: 20
<212> TYPE: DNA
<213> ORGANISM: Artificial Sequence
<220> FEATURE:
<223> OTHER INFORMATION: VJ558L forward primer

<400> SEQUENCE: 16
atgggatgga gctggatctt                                               20

<210> SEQ ID NO 17
<211> LENGTH: 20
<212> TYPE: DNA
<213> ORGANISM: Artificial Sequence
<220> FEATURE:
<223> OTHER INFORMATION: VJ558CL forward primer

<400> SEQUENCE: 17
atggaatgga gctgggtctt                                               20
```

<210> SEQ ID NO 18
<211> LENGTH: 26
<212> TYPE: DNA
<213> ORGANISM: Artificial Sequence
<220> FEATURE:
<223> OTHER INFORMATION: JH1-4 reverse primer

<400> SEQUENCE: 18
gagacdgtga shrdrgtbcc tksrcc                                         26

<210> SEQ ID NO 19
<211> LENGTH: 24
<212> TYPE: DNA
<213> ORGANISM: Artificial Sequence
<220> FEATURE:
<223> OTHER INFORMATION: lamin forward primer

<400> SEQUENCE: 19
gtatgaggcg gcactaaact ctaa                                           24

<210> SEQ ID NO 20
<211> LENGTH: 24
<212> TYPE: DNA
<213> ORGANISM: Artificial Sequence
<220> FEATURE:
<223> OTHER INFORMATION: lamin reverse genomic primer

<400> SEQUENCE: 20
gaagccactg aagaacacaa atag                                           24

<210> SEQ ID NO 21
<211> LENGTH: 24
<212> TYPE: DNA
<213> ORGANISM: Artificial Sequence
<220> FEATURE:
<223> OTHER INFORMATION: lamin reverse cDNA primer

<400> SEQUENCE: 21
tacgaaactc caagtcctca gtaa                                           24

<210> SEQ ID NO 22
<211> LENGTH: 53
<212> TYPE: DNA
<213> ORGANISM: Artificial sequence
<220> FEATURE:
<223> OTHER INFORMATION: recombinant polynucleotide

<400> SEQUENCE: 22
ttcggtacca taacttcgta taatgtatgc tatacgaagt tatgaattcg ccc           53

<210> SEQ ID NO 23
<211> LENGTH: 50
<212> TYPE: DNA
<213> ORGANISM: Artificial sequence
<220> FEATURE:
<223> OTHER INFORMATION: recombinant polynucleotide

<400> SEQUENCE: 23
acccttaata taacttcgta taatgtatgc tatacgaagt tattaggtct               50

GENETICALLY MODIFIED NON-HUMAN MAMMALS AND CELLS

RELATED APPLICATIONS

This application is a continuation of U.S. patent application Ser. No. 10/547,066, filed May 22, 2006, which is a national stage filing under 35 U.S.C. §371 of international application PCT/GB2004/000768, filed Feb. 26, 2004, which was published under PCT Article 21(2) in English, the entire contents of each of which are incorporated herein by reference.

This invention relates to genetically modified non-human mammals, in particular to genetically modified rodents such as mice, which do not encode any endogenous immunoglobulin heavy chain constant region locus polypeptide. The invention also relates to genetically modified non-human cells, particularly embryonic stem cells, especially rodent cells such as mouse cells, which do not encode any endogenous immunoglobulin heavy chain constant region locus polypeptide. The invention also relates to genetically modified non-human cells, particularly embryonic stem cells and genetically modified non-human mammals produced therefrom, and their use in the production of non-human mammals and cells from which all the endogenous immunoglobulin heavy chain constant region genes (from Cµ to Cα) have been deleted from the genome.

This invention further relates to genetically modified non-human mammals, in particular to genetically modified rodents such as mice, in which the deletion of the endogenous immunoglobulin heavy chain constant region genes has been used to allow insertion of other genes, such as exogenous immunoglobulin genes or their segments, to secure and allow immunoglobulin heavy chain locus specific gene expression. Additionally, the invention relates to the expression of such genes produced by such mammals, and the use of such mammals or cells thereof in the production of modified immune systems with particular emphasis on production of immunoglobulins or antibodies.

Furthermore the invention relates to non-human mammals without any endogenous constant region genes bred with compatible non-human mammals capable of expressing exogenous immunoglobulin genes either as introduced rearranged entities or entities in germ line configuration and on large chromosome fragments such as BACs, YACs and HACs (bacterial, yeast and human artificial chromosomes). The transgenes and transloci can be of human DNA.

Brüggemann et al (PNAS 1989; 86: 6709-6723) describe production of mice carrying a human heavy chain minilocus with unrearranged Ig variable (V), diversity (D) and joining (J) elements linked to a human heavy chain constant µ gene, which encodes the IgM immunoglobulin isotype. The foreign (human) immunoglobulin genes are inserted into the germline of the transgenic mice, with the result that the foreign insert is present in addition to the endogenous Ig genes. In these mice the foreign genes can rearrange to encode a repertoire of immunoglobulins of the IgM isotype.

The work by Brüggemann et al (ibid) is also described in U.S. Pat. No. 5,545,807 which relates to a method of producing an immunoglobulin obtained from cells or body fluid of a transgenic animal which has had inserted into its germline genetic material that encodes for at least part of an immunoglobulin of foreign origin or that can rearrange to encode a repertoire of immunoglobulins. Therein, it is suggested that "it may be convenient to use a host animal that initially does not carry genetic material encoding immunoglobulin constant regions so that the resulting transgenic animal will use only the inserted foreign genetic material when producing the immunoglobulins. This can be achieved either by using a naturally occurring mutant lacking the relevant genetic material or, by artificially making mutants e.g. in cell lines ultimately to create a host from which the relevant genetic material has been removed." However, no suggestion is made as to how to provide such an IgC-deficient host animal and the teaching focuses only on insertion of human genetic material; no example is given in which the endogenous Ig heavy chain constant region is deleted.

Targeted alterations have focussed on individual C-region genes but the removal of Cµ, Cδ or Cε has not significantly altered progression in B-cell development [1-3]. It seems that silencing of individual C-genes or replacement [4,5] has little effect on developmental progression due to their functional redundancy. Similarly, even though removal of the Eµ enhancer region reduced DNA rearrangement [6,7] and replacement of the α3' enhancer affected switching [8] these are only small perturbations almost negligible in immune development.

Preventing the use of H-chain C-region genes with a subsequent block in B-cell development has been achieved by two opposite approaches. Removal of the $J(joining)_H$ segments eliminated D(diversity)-J rearrangement [9,10] and the mice are devoid of Ig+ B-cells but continue to develop B220+ B-cell precursors present at somewhat reduced levels EP 0 463 151 discloses mice in which a 2.3 kb fragment of the endogenous mouse heavy chain locus, carrying the D and J1-4 genes, is removed and replaced (by homologous recombination) with a neomycin resistance gene. The endogenous mouse IgH C genes are present in the mouse, but because the D and J genes are absent, rearrangement of the locus cannot take place and expression of the endogenous IgH C genes is blocked, preventing production of a functional message encoding an IgH C subunit.

Kitamura et al [11] (Nature 1991; 350: 423-426) describe production of mice with a disrupted Cµ region (µMT mice). This was achieved by gene targeting, in which a 9 kb genomic fragment of Cµ and Cδ carrying a stop codon and flanked by a 5' neomycin resistance gene and a 3'HSV tk gene, was inserted into the membrane exons of Cµ using embryonic stem cells. The ES cells were used to generate chimaeric animals, which were bred to obtain mice heterozygous and then homozygous for the disrupted Cµ region. Mice homozygous for the disrupted Cµ transmembrane exon were Ig deficient. B-cell development is dependent on the expression of surface µ at the pre B-cell stage, but because expression of surface µ did not occur in mice with the disrupted Cµ region (µMT mutation), the development of B cells was arrested at the stage of pre-B-cell maturation and thus no mature or antibody secreting B-cells were produced.

In the lines with JH regions removed or with the disrupted Cµ exon some L-chain rearrangement occurs and it also appears that animals with disrupted Cµ transmembrane exon bred to homozygosity in different mouse strains can largely overcome the block in Ig expression. This was particularly pronounced in the Balb/c background which revealed IgG, IgA and IgE expression in homozygous knock-out animals [12,13] whilst in the original C57BL/6 background only IgA was selectively expressed which has been interpreted as remnant of an ancient perhaps more primitive immune system [14].

There is a desire to produce genetically modified non-human mammals, e.g. rodents such as mice, in which the endogenous IgH genes have been silenced, or removed, in order to produce antibodies of foreign origin, expressed from introduced genes.

A number of approaches have been used for silencing (i.e. disruption), or removal, of single endogenous Ig genes, combined with simultaneous introduction of one exogenous human gene.

Pluschke et al (J. Immunol. Methods 1998; 215 (1-2): 27-37) used a conventional gene targeting strategy (Stief et al., J. Immunol. 1994; 152: 3378) in embryonic stem cells to replace the mouse IgH constant gamma 2a (Cγ2a) gene segment with the human IgH constant gamma 1 (Cγ1); in addition to this, ES cells were generated in which the mouse IgL kappa gene segment was replaced with its human counterpart. The ES cells were used to generate chimaeric mice.

Zou et al (Science, 1993; 262, 1271-1274) describe a Cre-loxP recombination system that operates in mammalian cells and has been used for gene targeting experiments in the mouse to generate "clean" deletions of target genes in the germ line, as well as to inactivate genes in a conditional manner (based on regulated expression of Cre recombinase).

Cre is a 38 kDa recombinase protein from bacteriophage P1 which mediates intramolecular (excisive or inversional) and intermolecular (integrative) site specific recombination between loxP sites; for a review of the system refer to Sauer in Methods of Enzymology; 1993, Vol. 225, 890-900. A loxP site (the locus of crossing over) consists of two 13 bp inverted repeats separated by an 8 bp asymmetric spacer region. One molecule of Cre binds per inverted repeat, or two Cre molecules line up at one loxP site. The recombination occurs in the asymmetric spacer region. Those 8 bases are also responsible for the directionality of the site. Two loxP sequences in opposite orientation to each other invert the intervening piece of DNA, two sites in direct orientation dictate excision of the intervening DNA between the sites, leaving one loxP site behind. This precise removal of DNA can be used to eliminate genes (gene deletion) or to activate genes. The Cre-loxP system can also be used to introduce genes (gene introduction). A gene flanked by two loxP sites in a direct orientation is referred to as a "floxed gene".

Zou et al (Current Biology 1994; 4: (12) 1099-2003) describe use of the Cre-loxP system in mouse embryonic stem cells to replace the mouse gene Cγ1, which encodes the constant region of the heavy chain of IgG1 antibodies, with the corresponding human gene Cγ1. A targeting construct was generated in which a loxP site was cloned at the 3'end of the target gene sequence (in this instance the mouse Cγ1) and, at a position 5' of the target gene, an insertion was made of (from 5' to 3') a mutant gene of interest (in this instance human Cγ1), a loxP site, a negative selection marker (HSV-tk) and a positive selection marker (neo$^r$). In the construct the loxP sites were in direct orientation. The targeting construct was introduced by transfection into ES cells, transformants were selected on G418 by neomycin resistance. A Cre construct was introduced into the transformed cells to achieve transient expression of Cre. Recombination, that is excision of the sequence between the two loxP sites (encoding HSV-tk, neo$^r$ and the endogenous target gene mouse Cγ1), occurred only in those cells expressing Cre recombinase. The human Cγ1 sequence was situated outside the loxP sites and thus remained inserted within the mouse genome. Negative selection using acyclovir or gancyclovir was used to identify those cells in which the deletion had taken place, as only cells that do not express HSV-tk, i.e. those in which the endogenous mouse Cγ1 gene has also been deleted, were able to survive on those media.

Thus, Zou et al (1994) used the Cre-loxP system to introduce a human Cγ1 gene and then delete a single endogenous Ig heavy chain constant region gene, Cγ1. The exons encoding the transmembrane and cytoplasmic portions of the IgH mouse Cγ1 were not replaced by human sequences, these were retained to minimise the risk of disturbing membrane expression and signalling of the humanised IgG1 in the mouse. The introduced human Cγ1 gene was transmitted through the mouse germline and the resulting mutant mice were crossed with mice expressing kappa light chains with a human, instead of mouse constant region. Mice homozygous for both insertions produce humanised kappa chain bearing IgG1 antibodies.

Nicholson et al (J. Immunol. 1999; 6888-6906) produced mice that carry YAC based human Ig heavy and both κ and λ light chain transloci in a background in which the endogenous IgH and Igκ loci have been inactivated. Inactivation of the IgH locus was achieved using the Cμ (μMT mutant) mice described by Kitamura (1991) supra, Igκ expression was disrupted by insertion of a Neo cassette in the Cκ gene (Zou et al Eur J Immunol 1995, 25, 2154).

A technical problem addressed by this invention is the production of a non-human mammal, that is unable to express any of its endogenous IgH C genes and thus is immunodeficient. A particular problem addressed by the present invention is the production of a rodent, in particular a mouse, that is unable to express any of its 8 endogenous IgH C genes. To achieve this, it is necessary to generate a mutant non-human mammal, in particular a rodent such as a mouse, in which the endogenous heavy chain constant region genes are no longer present or not functionally active.

Accordingly the present invention provides a genetically modified non-human mammal or a genetically modified non-human mammalian cell characterised in that it does not comprise a nucleic acid sequence which itself encodes any endogenous immunoglobulin heavy chain constant region locus polypeptide. The invention also provides a genetically modified or transgenic mouse wherein the germ cells are free from the endogenous immunoglobulin C gene locus. The invention further provides a genetically modified transgenic mouse or the progeny thereof, wherein the somatic and germ cells are free from the endogenous immunoglobulin C gene locus.

In an aspect of the invention, the genetically modified mouse does not comprise a nucleic acid sequence which itself encodes any immunoglobulin heavy chain constant region locus polypeptide. In preferred genetically modified non-human mammals and cells of the invention, all immunoglobulin heavy chain constant (IgH C) region gene sequences are absent or partially absent from the genome. Preferably each of the endogenous IgH C region genes is absent; more preferably the entire endogenous C region (from Cμ to Cα) is absent.

Herein, endogenous is defined as authentic, native, not foreign and not modified by genetic engineering such as gene targeting or gene introduction.

Genetically modified non-human mammals or cells are obtainable by targeted deletion of all or essentially all endogenous IgH C gene sequences. The deletion can be of all endogenous IgH C region genes and intervening sequences (complete exon/intron removal or clean deletion) or essentially all endogenous IgH C sequences by deletion of an extensive part of the endogenous IgH C region gene sequence such that expression of any of the IgH C genes is prevented. Targeted deletion can be performed by a recombination-excision process, for example by Cre-loxP recombination. Thus the invention further provides a genetically modified or transgenic non-human mammal as described herein or a genetically modified or transgenic non-human mammalian cell preferably an embryonic stem cell as described herein, obtainable by a site specific recombination method, preferably by a Cre-loxP recombination method.

In site specific recombination methods for targeted deletion, a region of nucleic acid sequence flanked by two site specific recombination sequences is excised; following excision, a single site specific recombination sequence remains within the genome. It is preferred that the site specific recombination sequence is a non-endogenous site specific recombination (NESSR) site. Several methods can be used to produce a non-human mammalian cell in which the target sequence for deletion, i.e. the endogenous IgH C locus, is flanked by NESSR sites. In one such method, NESSR sites are sequentially integrated into the genome of a non-human mammalian cell, preferably an embryonic stem cell, so that a NESSR site is first introduced to a cell and integrated at one end of the target sequence and secondly a NESSR site is introduced and integrated at the other end of the target sequence. In an alternative method, the NESSR sites are introduced simultaneously to the cell for integration at each end of the target sequence. Cells with a NESSR site at one or other end of the target sequence can be used to produce genetically modified non-human mammals with NESSR sequences present within the genome at one or other end of the target sequence. A non-human mammal having a single NESSR site at one end of the IgH C locus target sequence can be bred with non-human mammal having a NESSR site at the other end of the IgH C locus target sequence, to produce progeny with NESSR sites flanking the target sequence. Cells with NESSR sites flanking the IgH C locus target sequence can be used to produce genetically modified non-human mammals with NESSR sequences present within the genome flanking the endogenous IgH C locus.

The present invention provides a genetically modified mouse having at least one non-endogenous site-specific recombination sequence present within the genome downstream of, or within the last gene of the IgH C locus and/or upstream of, or within the first gene of the IgH C locus. In a preferred embodiment two NESSR sites, preferably loxP sites, are integrated within the genome downstream of, or within the last gene of the IgH C locus and upstream of, or within the first gene of the IgH C locus.

An NESSR site may be present upstream at a position adjacent to the first gene of the IgH C locus and/or downstream at a position adjacent to the last gene of the IgH locus. By "adjacent to", it is meant that the NESSR site is positioned 5' or 3' of the start of the first gene, or end of the last gene of the IgH C locus. This implies that the first or last gene of the IgH C locus is the coding region nearest to the NESSR.

The invention provides a genetically modified non-human mammal, or a genetically modified non-human mammalian cell as described herein having NESSR sites, which are preferably loxP sites, flanking the IgH C region genes, or inserted into the genes at each end of the IgH C region genes.

The invention provides a genetically modified non-human mammal, or a genetically modified non-human mammalian cell in which the endogenous IgH C genes are absent as described herein and a non-endogenous site specific recombination (NESSR) site is present within the genome, preferably the non-endogenous site specific recombination site is a loxP recombination site.

It is preferred that the endogenous IgH C genes are deleted, but at least part of at least one endogenous IgH C enhancer sequence is retained. This has the advantage of improving expression of foreign genes when these are inserted at the locus and allows locus specific regulation of site-specifically introduced genes, (e.g. by using Cre-loxP insertion utilising the remaining loxP site in the deleted IgH C gene cluster). Retention of at least part of the endogenous J-C-intronic enhancer sequence and/or at least part of the α3' enhancer sequence is particularly preferred.

In a genetically modified mouse of the invention, one or more endogenous Ig H variable region, D and/or J segment nucleic acid sequences may be present. In one embodiment it is particularly preferred that endogenous IgH variable region and D segment and J segment nucleic acid sequences are present. In an alternative embodiment an exogenous variable region, preferably a mammalian variable region, more preferably a human variable region, is present.

A genetically modified mouse of the invention may comprise one or more selectable marker(s) integrated within the genome.

A selectable marker may be positioned upstream of, or downstream of, a non-endogenous site specific recombination sequence. At least one selectable marker may be integrated within the genome upstream of, and/or downstream of, at least one non-endogenous site specific recombination sequence.

In a preferred embodiment, the invention provides a genetically modified non-human mammal, or a genetically modified non-human mammalian cell, having a selectable marker integrated upstream or downstream of the first and/or last endogenous IgH C gene and/or upstream or downstream of a loxP sequence.

The selectable marker is preferably one or more of: a neomycin resistance gene; a puromycin resistance gene; a hygromycin gene or a herpes simplex virus thymidine kinase gene.

The invention further provides a genetically modified non-human mammal, or a genetically modified non-human mammalian cell as described herein characterised in that a different selectable marker is integrated at each end of the IgH C region.

Thus the invention also provides a non-human mammal or non-human mammalian cell, preferably a rodent cell, more preferably a mouse cell, most preferably a mouse embryonic stem cell, free from the endogenous immunoglobulin heavy chain locus and comprising one or more gene(s) encoding a selectable marker.

A genetically modified non-human mammal of the invention can be rodent, murine, ovine, porcine, equine, canine, feline or the like, but is preferably a rodent, more preferably murine, most preferably a mouse. A genetically modified non-human mammalian cell of the invention may be an embryonic stem cell or an oocyte; and is preferably a rodent, murine, ovine, porcine, equine, canine or feline cell, or the like, preferably a rodent cell, more preferably a murine cell, most preferably a mouse cell. Mice are particularly preferred as their immune repertoire is extensive and they are easy to handle and breed.

The present invention provides a mouse in which all 8 endogenous heavy chain constant region immunoglobulin genes (μ, δ, γ3, γ1, γ2a, γ2b, ε and α) are absent, or partially absent to the extent that they are non-functional, or in which genes δ, γ3, γ1, γ2a, γ2b and ε are absent and the flanking genes μ a and α are partially absent to the extent that they are rendered non-functional, or in which genes μ, δ, γ3, γ1, γ2a, γ2b and ε are absent and α is partially absent to the extent that it is rendered non-functional, or in which δ, γ3, γ1, γ2a, γ2b, ε and α are absent and μ is partially absent to the extent that it is rendered non-functional.

By partially absent it is meant that the endogenous IgH constant region gene sequence has been deleted or disrupted to the extent that no functional endogenous IgH C gene product is encoded at the IgH C locus, i.e. that no functional endogenous IgH C gene product could be expressed from the locus.

The present invention further provides a non-human mammalian embryonic stem (ES) cell characterised in that the endogenous Ig heavy chain constant region genes are absent or partially absent. Preferably all of the endogenous IgH C region genes are absent; more preferably all the known endogenous IgH C genes are absent.

In a preferred embodiment the ES cell is a deletion mutant mouse embryonic stem cell in which all 8 endogenous heavy chain constant region immunoglobulin genes μ, δ, γ3, γ1, γ2a, γ2b, ε and α are absent or partially absent to the extent that they are non-functional, or in which genes δ, γ3, γ1, γ2a, γ2b and ε are absent and the flanking genes μ and α are partially absent to the extent that they are rendered non-functional, or in which genes μ, δ, γ3, γ1, γ2a, γ2b and ε are absent and α is partially absent to the extent that it is rendered non-functional, or in which genes δ, γ3, γ1, γ2a, γ2b, ε and α are absent and μ is partially absent to the extent that it is rendered non-functional.

The deletion mutant non-human mammal, preferably a rodent, more preferably a mouse, can be bred with a compatible non-human mammal that is able to express one or more functionally active IgH C genes, preferably one or more functionally active human IgH C genes, e.g. a deletion mutant mouse can be bred with a mouse capable of expressing one or more functionally active human IgH C genes. The heterozygous progeny (F1) of this cross can be inter-bred to produce heterozygous and homozygous progeny (F2) of a non-human mammal, preferably a mouse, that is not able to express the endogenous IgH C genes and instead is able to express only foreign, preferably human, IgH C gene(s).

As shown in other Ig knock-out mouse strains expressing Ig transgenes, the presence of mouse C genes can result in the production of chimeric human (i.e. foreign)—mouse Ig chains by trans-switching or trans-splicing mechanisms that bring gene segments on different chromosomal locations together (reviewed in Brüggemann and Taussig, Curr. Opin. Biotechn., 8, 455-458, 1997). Thus, an advantage of having deleted the entire or essentially the entire endogenous IgH C gene region is that in F2 progeny, having and expressing an introduced, e.g. exogenous IgH gene or locus, the endogenous IgH C gene locus cannot be re-activated to produce unconventional switch or splice products. Accordingly, an advantage of producing a non-human animal with silenced endogenous Ig genes and introduced human Ig genes is that no mixed molecules (e.g. mouse IgH and human IgL) can be produced and thus immunisation of that animal allows the production of specific fully human antibodies.

The invention provides a genetically modified non-human mammal derived from a genetically modified non-human mammal as described herein, or from a genetically modified non-human cell as described herein, and provides a genetically modified non-human cell derived from a genetically modified non-human mammal as described herein.

The invention provides a method for producing a genetically modified non-human cell comprising:

(a) (i) transfecting a non-human cell with a targeting construct for integration upstream of, or within the first IgH C gene of the IgH C locus, said targeting construct comprising a non-endogenous site specific recombination sequence and a selectable marker, selecting for a cell in which the selectable marker is present and screening said cell for integration of the recombination sequence, and, (ii) transfecting a cell produced in (a)(i) with a targeting construct for integration downstream of, or within the last IgH C gene of the IgH C locus, said targeting construct comprising a selectable marker and a non-endogenous site-specific recombination sequence, selecting for a cell in which the selectable marker is present and screening said cell for integration of the recombination sequence; or, (b) (i) transfecting a non-human cell with a targeting construct for integration downstream of, or within the last IgH C gene of the IgH C locus, said targeting construct comprising a non-endogenous site-specific recombination sequence and a selectable marker, selecting for a cell in which the selectable marker is present, and screening said cell for integration of the recombination sequence, and, (ii) transfecting a cell produced in (b)(i) with a targeting construct for integration upstream of, or within the first IgH C gene of the IgH C locus, said targeting construct comprising a non-endogenous site-specific recombination sequence and a selectable marker, selecting for a cell in which the selectable marker is present, and screening said cell for integration of the recombination sequence; or, co-transfecting a non-human cell with a targeting construct for integration upstream of, or within the first IgH C gene of the IgH C locus and with a targeting construct for integration downstream of, or within the last IgH C gene of the IgH C locus, each of said targeting constructs comprising a non-endogenous site specific recombination sequence and each having a selectable marker, selecting for a cell in which the selectable marker(s) is/are present, and screening said cell for integration of the recombination sequence; and optionally, (d) providing to a cell obtained in (a)(ii), (b)(ii) or (c) a recombinase active at the non-endogenous site-specific recombination sequence and screening for deletion events.

The recombinase in optional step (d) can be provided by an expression vector, i.e. by introduction of an expression vector into the cell. In a preferred method, the non-endogenous site-specific recombination sequence is a loxP site and in optional step (d), the recombinase is a Cre recombinase.

It is preferred that the genetically modified non-human cell is an embryonic stem cell or an oocyte. The genetically modified non-human cell can be a rodent cell, more preferably a mouse cell.

Any suitable cloning vector may be used to generate the targeting construct, cloning strategies are described by Sambrook, Fritsch and Maniatis in Molecular Cloning, A Laboratory Manual, Cold Spring Harbor Laboratory Press, 1989. Desirably, the targeting construct may carry one or more marker genes; suitable markers are known, especially suitable are those that allow for positive selection. Of particular interest is the use of the gene for neomycin phosphotransferase ("neo"), which confers resistance to G418, also suitable is the puromycin resistance gene ("puro") or the hygromycin resistance gene; neomycin and/or puromycin resistance genes are preferred.

In the targeting construct, upstream and/or downstream from the target gene, may be a gene which provides for identification of whether a homologous double crossover has occurred (negative selection). The Herpes simplex virus thymidine kinase gene (HSV-tk) may be used as a negative selection marker, since cells producing thymidine kinase may be killed by acyclovir or gancyclovir.

Once a targeting construct has been prepared and any undesirable sequences removed, the construct can be introduced into the target cell, for example an ES cell or an oocyte. Any convenient technique for introducing the DNA into the target cell may be employed. For conventional gene targeting (usually constructs up to 20 kb), DNA is most frequently introduced by electroporation (see Zou et al., Eur. J. Immunol., 25, 2154-62, 1995) whilst for secondary modifications, such as Cre-loxP mediated integration, electroporation can be used for integration of smaller constructs and other methods such as lipofection and yeast spheroplast/cell fusion for YACs (yeast artificial chromosomes) and calcium phosphate-mediated DNA transfer for chromosome-fragments or mammalian artificial chromosomes which would allow integration of several 100 kb up to the Mb range. Thus, electroporation is the preferred technique for introduction of small DNA fragments (up to 50 kb) into the target cell, the other methods listed are suitable and perhaps advantageous for the introduction of larger DNA sequences (>50 kb).

After transformation or transfection of the target cells, they may be selected by means of positive and/or negative markers. As previously indicated, positive markers such as neomycin and/or puromycin resistance genes can be used. Those cells with the desired phenotype may then be further analysed by restriction analysis, electrophoresis, Southern blot analysis, PCR, or the like.

PCR may also be used to detect the presence of homologous recombination. PCR primers can be used that are complementary to a sequence within the targeting construct, and complementary to a sequence outside the construct and at the target locus. DNA molecules are obtained in the PCR reaction only when both the primers are able to bind to the complementary sequences, i.e. only if homologous recombination has occurred. Demonstration of the expected size fragments, verified by sequencing, supports the conclusion that homologous recombination has occurred.

While the presence of the marker gene in the genome indicates that integration has taken place, it is necessary to determine whether homologous integration has occurred. Methods for achieving this are known in the art, such as using DNA analysis by Southern blot hybridisation to establish the location of the integration. By employing probes for both the insert and the sequences at the 5' and 3' regions distant to the flanking region where homologous integration would occur, it can be shown that homologous targeting has been achieved. An advantage is that external probes adjacent to the targeting DNA and newly introduced restriction sites, for example by a selectable marker gene, can be used for identification of the targeted alteration Thus screening, preferably by PCR, can be used to confirm integration of NESSR sites such as loxP sites in the correct position, on the same allele and in the correct (direct) orientation to allow gene removal by deletion. Screening using methods such as PCR can also be used to detect deletion events.

An embryonic stem cell as described herein, e.g. obtainable by the above method, can be used for the production of a genetically modified non-human mammal.

The above-described processes may be performed first to inactivate the constant heavy chain loci in an embryonic stem cell, the cells may then be injected into a host blastocysts and developed into a chimaeric animal Suitable methods are described, for example, in Hogan et al, (Hogan, B., Beddington, R., Costantini, F., and Lacy, E. (1994). Manipulating the Mouse Embryo: A Laboratory Manual. Cold Spring Harbour Press NY). Chimaeric animals are bred to obtain heterozygous hosts. Then, by breeding of the heterozygous hosts, a homozygous host may be obtained.

Accordingly, the invention provides a method for producing a genetically modified non-human mammal characterised in that an embryonic stem cell as described herein is introduced into a host blastocyst and developed into a chimaeric animal.

This can be achieved by a method characterised by:

(a) introducing a non-human mammal embryonic stem cell as described herein into a compatible non-human mammal blastocyst, and (b) transplanting the blastocyst obtained in (a) into a compatible non-human mammalian foster mother to obtain a chimaeric non-human mammal, and optionally, screening for the selectable marker(s), and/or non-endogenous site specific recombination sequence(s), and/or for deletion of all or essentially all endogenous IgH C gene sequences.

A chimaeric non-human mammal produced by these methods can be bred to obtain heterozygous progeny. The heterozygous progeny can be inter-bred to obtain homozygous progeny.

The present invention also provides a method for producing a genetically modified non-human mammal according to the invention comprising:

(a) injecting a non-human mammalian ES cell clone having two integrated loxP sites as described herein into a non-human mammalian blastocyst, (b) transplanting the blastocyst into a compatible non-human mammalian foster mother to obtain a progeny chimaeric non-human mammal, (c) optionally screening for loxP, (d) breeding the progeny to obtain a non-human mammal having two integrated loxP sites on the same allele, (e) cross-breeding a non-human mammal having two integrated loxP sites with a compatible Cre expressing non-human mammal, (f) screening the progeny for deletion mutants, preferably by PCR, or (g) generating genetically modified non-human mammals, e.g. mice, with two integrated loxP sites on one allele, or on one locus or on 2 separate alleles or loci, by cross breeding of mice derived either by transgenesis or the ES cell route, (h) inter- or intra-allelic locus deletion upon Cre expression.

The invention also provides a method for producing a genetically modified non-human mammal characterised by cross-breeding a genetically modified non-human mammal homozygous for integration of a non-endogenous site-specific recombination sequence upstream of, or within the first IgH C gene of the IgH C locus with a compatible genetically modified non-human mammal homozygous for integration of a non-endogenous site-specific recombination sequence downstream, or within the last IgH C gene of the IgH C locus, to obtain heterozygous progeny and optionally interbreeding the heterozygous progeny to obtain progeny homozygous for both integrations.

The progeny homozygous for both integrations can be cross-bred with a compatible non-human mammal capable of expressing a recombinase active at the non-endogenous site specific recombination sequence to obtain progeny; with IgH C gene deletion, which optionally can be screened using suitable methods to detect IgH C gene deletion.

The non-endogenous site specific recombination sequence (s) can be loxP sites and the recombinase a Cre recombinase.

Progeny heterozygous or homozygous for loxP at both loci can be cross-bred with a compatible non-human mammal capable of expressing Cre recombinase to obtain a progeny non-human mammal that does not comprise a nucleic acid sequence which itself encodes any endogenous Ig heavy chain constant region locus polypeptide on one or both alleles.

A transgenic non-human mammal capable of expressing Cre recombinase may be prepared by microinjection of linearised Cre plasmid into male pronucleus of F1 non-human mammal embryos to produce Cre expressing non-human mammal strain.

Using methods of the invention described herein a genetically modified non-human mammal can be obtained that does not comprise a nucleic acid sequence which itself encodes any endogenous Ig heavy chain constant region polypeptide.

The invention provides a method for producing a genetically modified non-human mammal capable of expressing one or more exogenous genes, characterised by breeding a genetically modified non-human mammal that does not comprise a nucleic acid sequence which itself encodes any endogenous immunoglobulin heavy chain constant region locus polypeptide, with a compatible non-human mammal that encodes and is capable of expressing one or more exogenous gene(s), to obtain progeny heterozygous for the one or more exogenous gene(s), and optionally inter-breeding the heterozygous progeny to produce progeny homozygous for the one or more exogenous gene(s).

An exogenous gene is a gene which is foreign, i.e. non-native, to the host mouse.

Thus the invention may be used to produce a non-human mammal, that is preferably a rodent, more preferably a mouse, that is capable of expressing foreign, preferably human immunoglobulin gene(s), by breeding the genetically modified non-human mammal, as defined herein that is unable to express functionally active (endogenous) IgH C genes, with a compatible non-human mammal, preferably a rodent, more preferably a mouse, that is able to express one or more functionally active foreign, preferably human IgH C genes. This enables inter-species gene/locus exchange to produce selected progeny (heterozygous or homozygous) with one or more functionally active exogenous, preferably human gene(s) of the desired traits in a background where the corresponding genes of the non-human mammal are silenced or removed.

A method is provided for producing a genetically modified mouse capable of expressing one or more exogenous gene(s) comprising introduction of one or more exogenous gene(s) into a non-human mammalian cell as described herein that does not comprise a nucleic acid sequence which itself encodes any endogenous immunoglobulin heavy chain constant region polypeptide. It is preferred that the non-human mammalian cell is an embryonic stem cell or an oocyte. When the non-human mammalian cell is an ES cell, it is preferred that the one or more exogenous gene(s) are introduced by transfection. When the non-human mammal cell is an oocyte (egg cell) it is preferred that the one or more exogenous gene(s) are introduced by DNA micro-injection. Preferably the one or more exogenous gene(s) are inserted into the genome of the mouse, most preferably the one or more exogenous gene(s) are inserted into a non-endogenous site specific recombination sequence.

An alternative method for producing a genetically modified non-human mammal capable of expressing one or more exogenous gene(s) is provided, that comprises cross-breeding a non-human mammal that does not comprise a nucleic acid sequence which itself encodes any endogenous immunoglobulin heavy chain constant region polypeptide with a compatible transgenic mammal having one or more exogenous gene(s) associated with or flanked by a non-endogenous site specific recombination sequence and having a recombinase active at the non-endogenous site specific recombination sequence to obtain progeny and optionally screening the progeny for insertion of the one or more exogenous gene(s).

In the above methods for producing a genetically modified non-human mammal or genetically modified non-human mammalian cell, capable of expressing one or more exogenous genes, it is preferred that the non-endogenous site specific recombination sequence is a loxP sequence and insertion is by Cre-lox P integration. The genetically modified non-human mammal is preferably a rodent, more preferably a mouse.

In order to provide for the production of xenogeneic (exogenous) binding proteins, (e.g. foreign antibody proteins) in a host, it is necessary that the host be competent to provide the necessary enzymes and other factors involved with the production of antibodies (e.g. the cellular recombination machinery), while lacking the endogenous genes for the expression of the heavy IgC sub-units of immunoglobulins and thus not able to express the remaining V, D and J segments after DNA rearrangement. Thus, those enzymes and other factors associated with germ line re-arrangement, splicing, somatic mutation, and the like are preferably functional in the host. However, a functional natural region comprising the various exons associated with the production of endogenous immunoglobulin heavy chain constant regions will be absent/deleted in certain embodiments of the invention.

In a deletion and replacement strategy, the exogenous genetic material for insertion may be produced from a mammalian source, preferably a human source, or may be produced synthetically. The material may code for at least part of a known immunoglobulin or may be modified to code for at least part of an altered immunoglobulin. Suitable techniques for these processes are well known.

In the case of the deletion and replacement strategy, where the xenogeneic DNA insert is large, complete Ig loci (1-3 Mb) could be inserted. The use of the Cre-loxP replacement strategy would then allow locus removal and insertion of a different locus.

The exogenous gene or genes is preferably an Ig H gene or Ig H genes, more preferably an IgH C gene or IgH C genes. The exogenous gene or genes can be a human gene or human gene(s), preferably the exogenous gene(s) are human Ig heavy chain constant region genes, more preferably a human Ig heavy chain constant region locus, or a human Ig heavy chain locus, having V, D, J and/or C regions.

In the human, the immunoglobulin heavy chain locus is located on chromosome 14. In the 5'-3' direction of transcription, the locus comprises a large cluster of variable region genes ($V_H$), the diversity (D) region genes, followed by the joining ($J_H$) region genes and the constant ($C_H$) gene cluster. The size of the locus is estimated to be about 2,500 kilobases (kb). During B-cell development, discontinuous gene segments from the germ line IgH locus are juxtaposed by means of a physical rearrangement of the DNA. In order for a functional heavy chain Ig polypeptide to be produced, three discontinuous DNA segments, from the $V_H$, D, and $J_H$ regions must be joined in a specific sequential fashion; $V_H$ to $DJ_H$, generating the functional unit $V_H DJ_H$. Once a $V_H DJ_H$ has been formed, specific heavy chains are produced following transcription of the Ig locus, utilising as a template the specific $V_H DJ_H C_H$ unit comprising exons and introns. There are two loci for Ig light chains, the κ locus on human chromosome 2 and the λ locus on human chromosome 22. The structure of the IgL loci is similar to that of the IgH locus, except that the D region is not present. Following IgH rearrangement, rearrangement of a light chain locus is similarly accomplished by $V_L$ and $J_L$, joining of the κ or λ chain. The sizes of the λ and κ loci are each 1-3 Mb. Expression of rearranged IgH and an Igκ or Igλ light chain in a particular B-cell allows for the generation of antibody molecules.

The human Ig heavy chain locus V, D, J and/or C regions can be in germline configuration, or can be productively arranged. In germline configuration the exons are spaced by intervening sequences thus gene sequence must be rearranged for expression of the gene(s). When productively arranged, intervening sequences have been removed from the gene sequence and thus re-arrangement of gene sequence is not required for expression of the gene(s).

The invention provides a mouse capable of expressing one or more exogenous genes, obtainable by a method described herein and provides the use of a mouse in the production of exogenous immunoglobulin, preferably human immunoglobulin.

An exogenous immunoglobulin is an immunoglobulin which is non-native to the host mammal or cell in which it is produced; in some embodiments of the invention it is preferred that the exogenous immunoglobulin comprises a mammalian variable region which is non-native to the host mammal or cell in which it is produced, more preferably the mammalian variable region is a human variable region.

It has been found that a transgenic non-human mammal can produce chimaeric or foreign immunoglobulin (derived from inserted exogenous genetic material) in response to an immunogen subsequently introduced to the transgenic non-human mammal. Accordingly, by introducing foreign, e.g. human, genetic material encoding for substantially the entire species-specific regions of an immunoglobulin it may be possible to stimulate the transgenic non-human mammal to produce foreign immunoglobulin to any antigen introduced to the animal. The transgenic animal could thus provide a highly useful, convenient and valuable source of human immunoglobulins to a large range of antigens. Furthermore, there would be no interference due to endogenous IgH C polypeptide being simultaneously expressed.

Accordingly the present invention provides a method for production of an immunoglobulin comprising use of a mouse of the invention, which is capable of expressing one or more exogenous genes, the immunoglobulin being an exogenous immunoglobulin with respect to the host mammal or cell in which it is produced. In a preferred aspect the exogenous immunoglobulin comprises a mammalian variable region that is non-native to the host mammal or cell in which it is produced, more preferably the mammalian variable region is a human variable region. In another preferred aspect the exogenous immmunoglobulin is a human immunoglobulin When a non-human mammal is employed in a use or method for production of an exogenous immunoglobulin, the non-human mammal is a preferably a rodent, more preferably a mouse.

When a non-human mammalian cell is employed in a use or method for production of an exogenous immunoglobulin, the non-human mammalian cell is a preferably a rodent cell, more preferably a mouse cell.

The present invention also provides an immunoglobulin obtainable or obtained by a use or method of the invention for the production of an exogenous immunoglobulin.

The present invention also provides a human immunoglobulin obtainable or obtained by a use or method of the invention for the production of an exogenous immunoglobulin.

Further provided is an immunoglobulin for use as a medicament, said immunoglobulin being obtainable or obtained by a use or method of the invention for the production of an exogenous immunoglobulin. Yet further provided is the use of an immunoglobulin in the manufacture of a medicament, said immunoglobulin being obtainable or obtained by a use or method of the invention for the production of an exogenous immunoglobulin. Also provided is a medicament composition comprising an immunoglobulin according to the invention and a pharmaceutically acceptable excipient.

(half of the mice with the correct coat colour did not have the target modification) it seems that the two targeted integrations are on one allele but that cross-over frequently separated the two regions.

Figure 13:
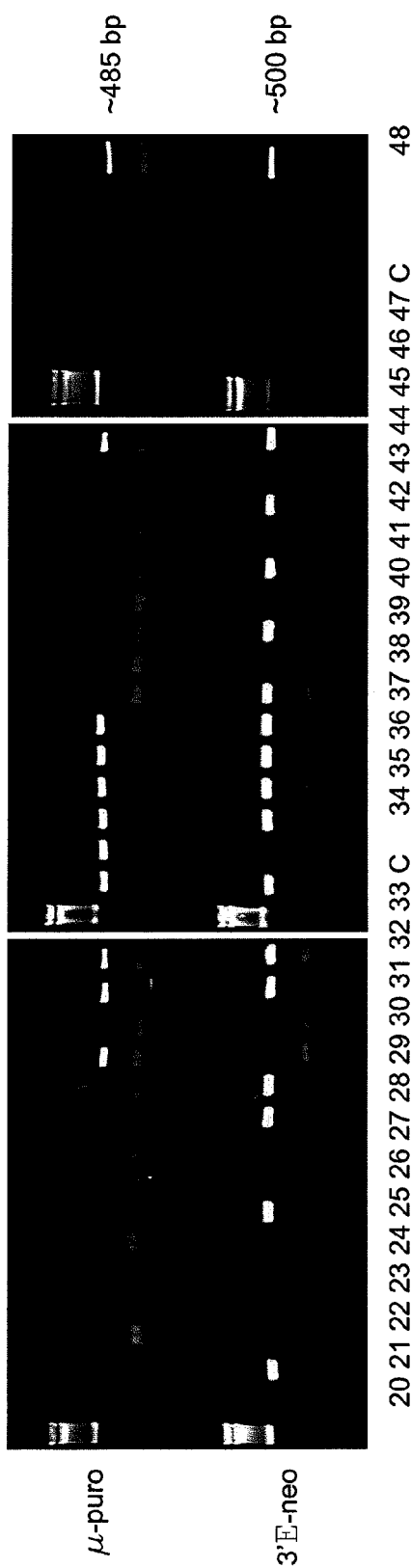

FIG. 13 shows the results of PCR analysis of a larger number of potential germline transmission mice (selected on the basis of coat colour) which resulted in identification of 7 mice that carry both targeting events 3'E and μ. Of 51 mice, 22 were negative, 14 positive for targeted integration in 3'E, 7 positive for targeted integration in μ and 7 were positive for both 3'E and μ targeting events.

Figure 14:
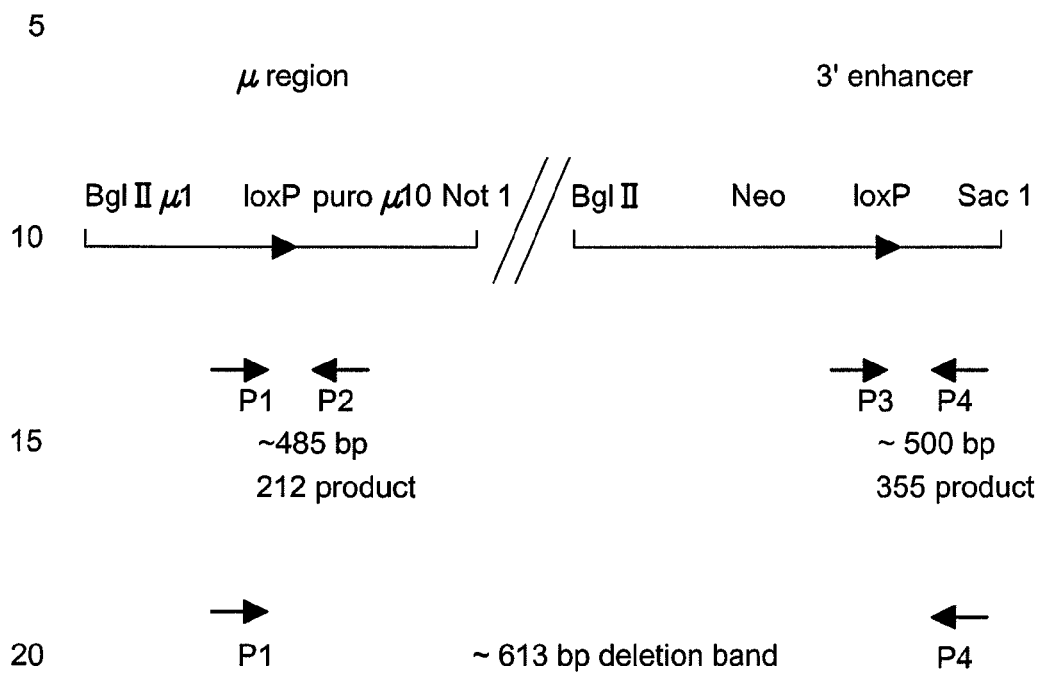

FIG. 14 shows the scheme for PCR analysis of IgHC knock out (deletion) mice.

Figure 15:
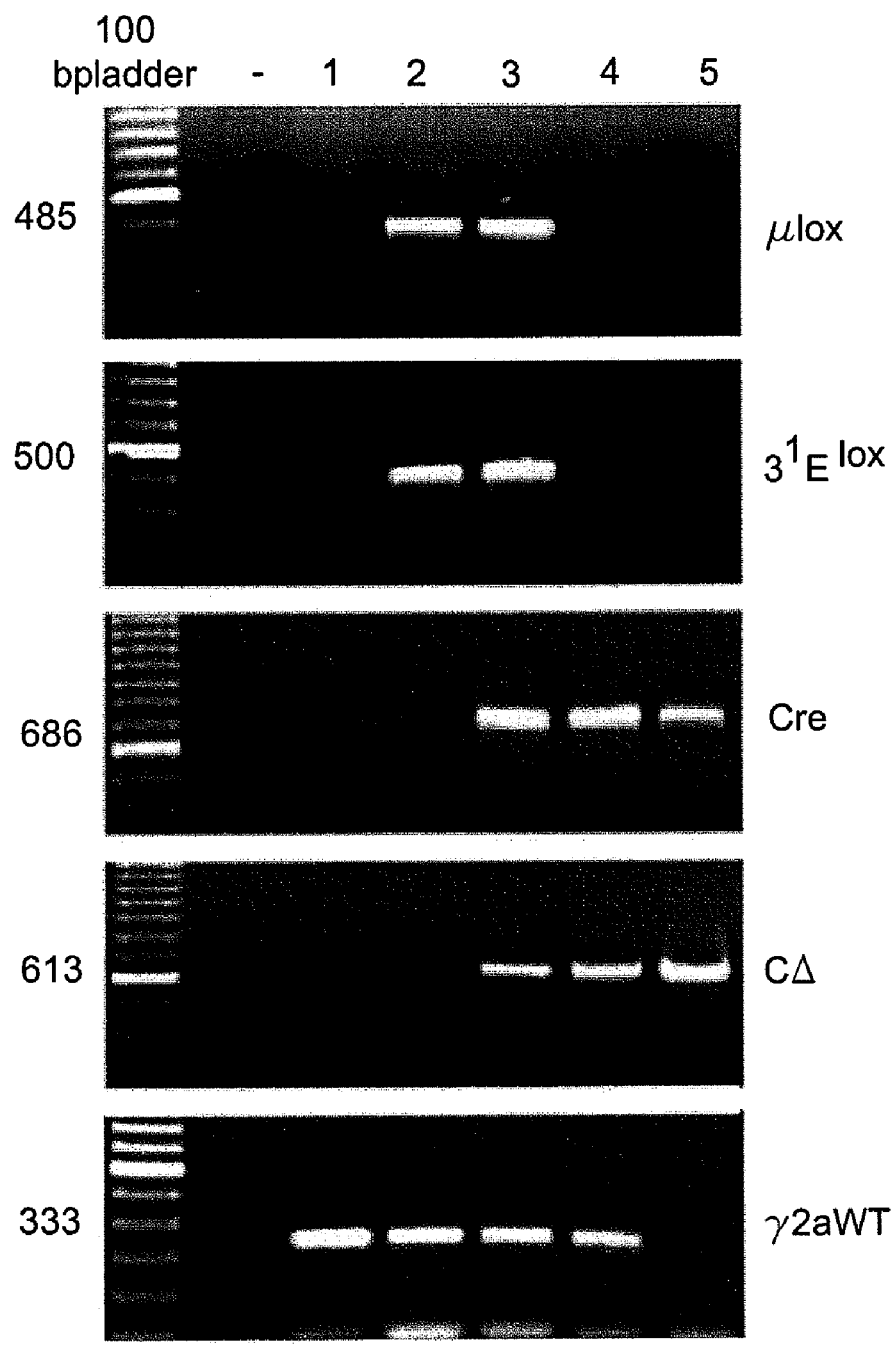
Figure 16A:
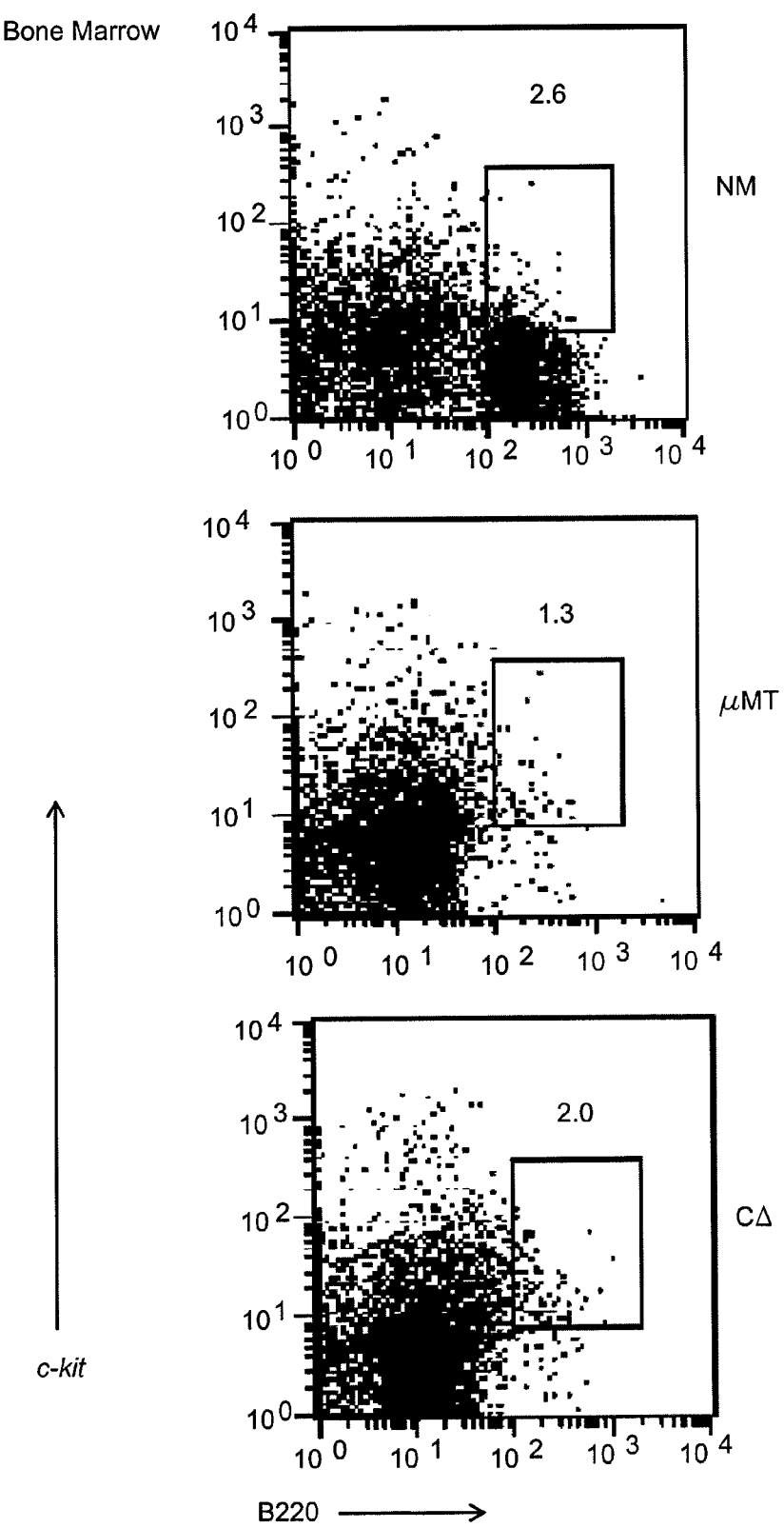
Figure 16B:
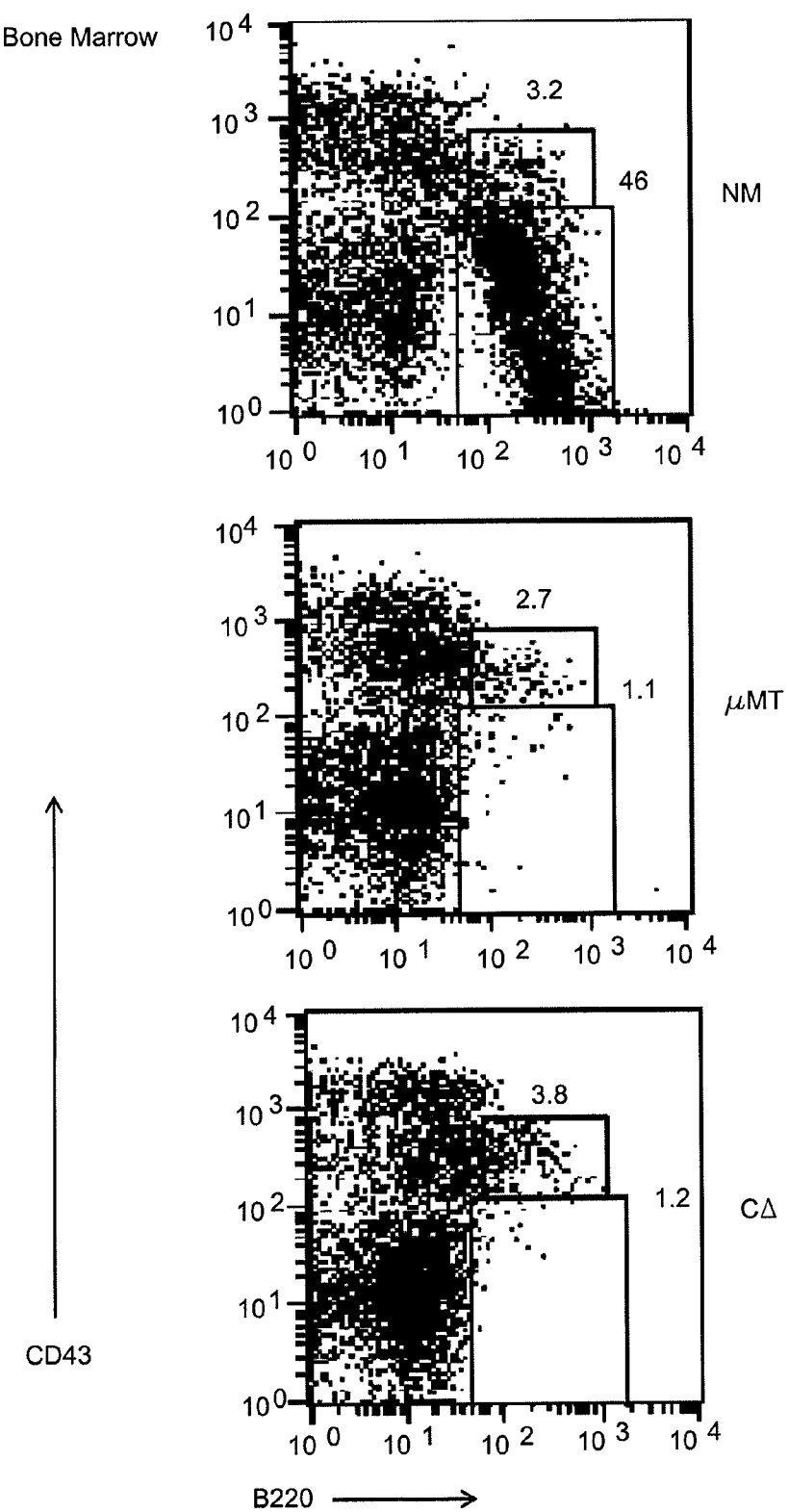
Figure 16C:
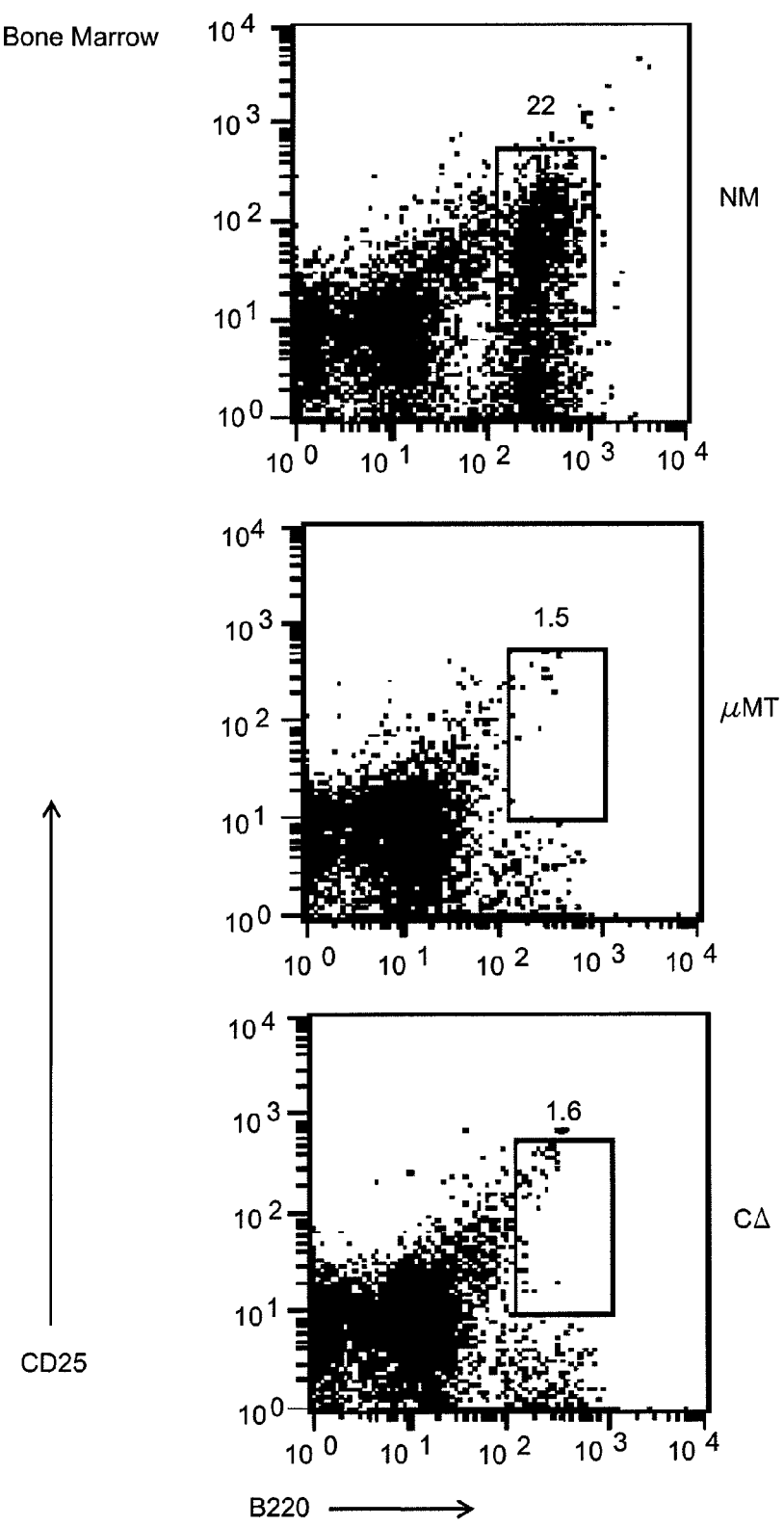
Figure 16D:
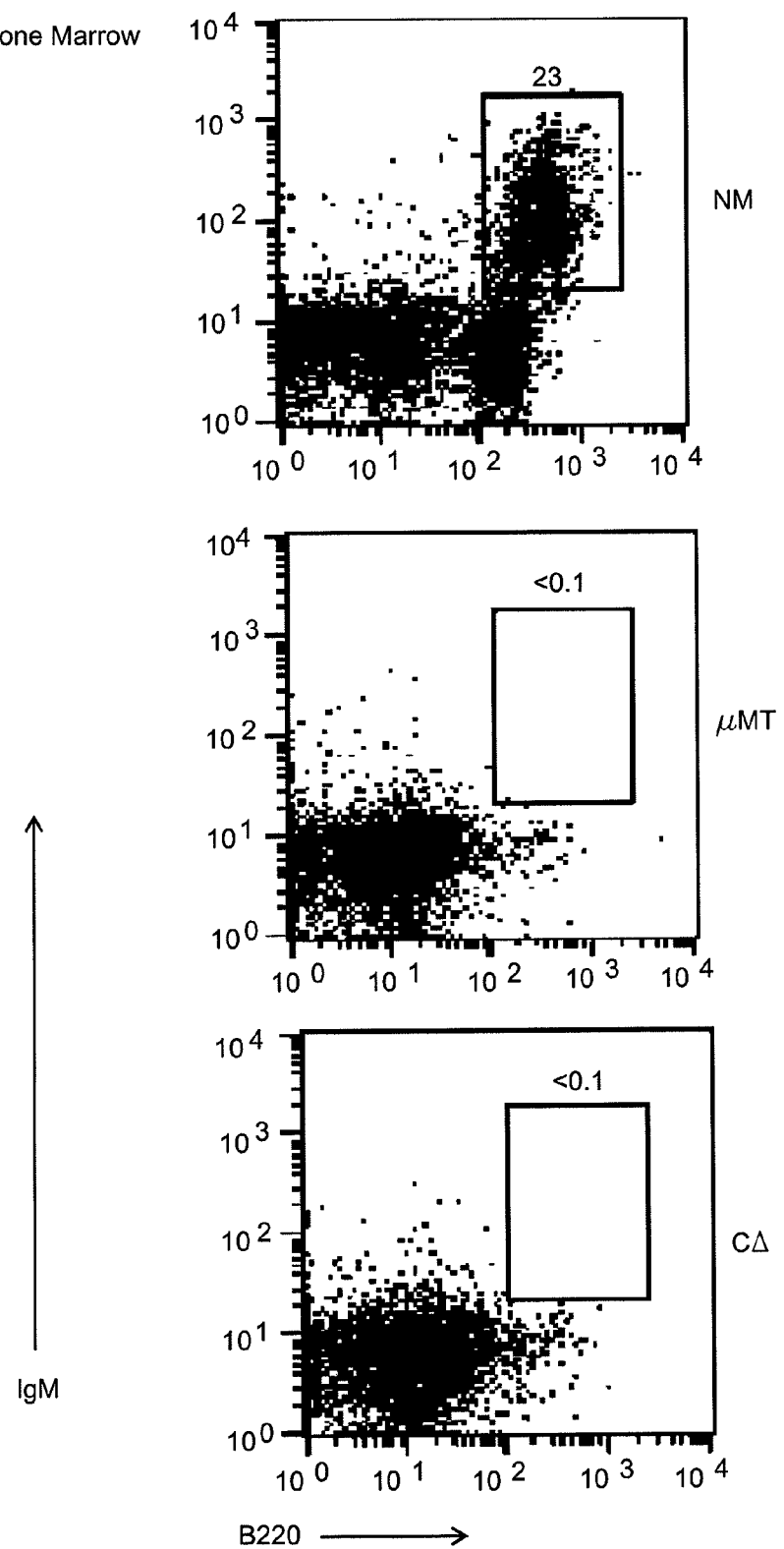
Figure 16E:
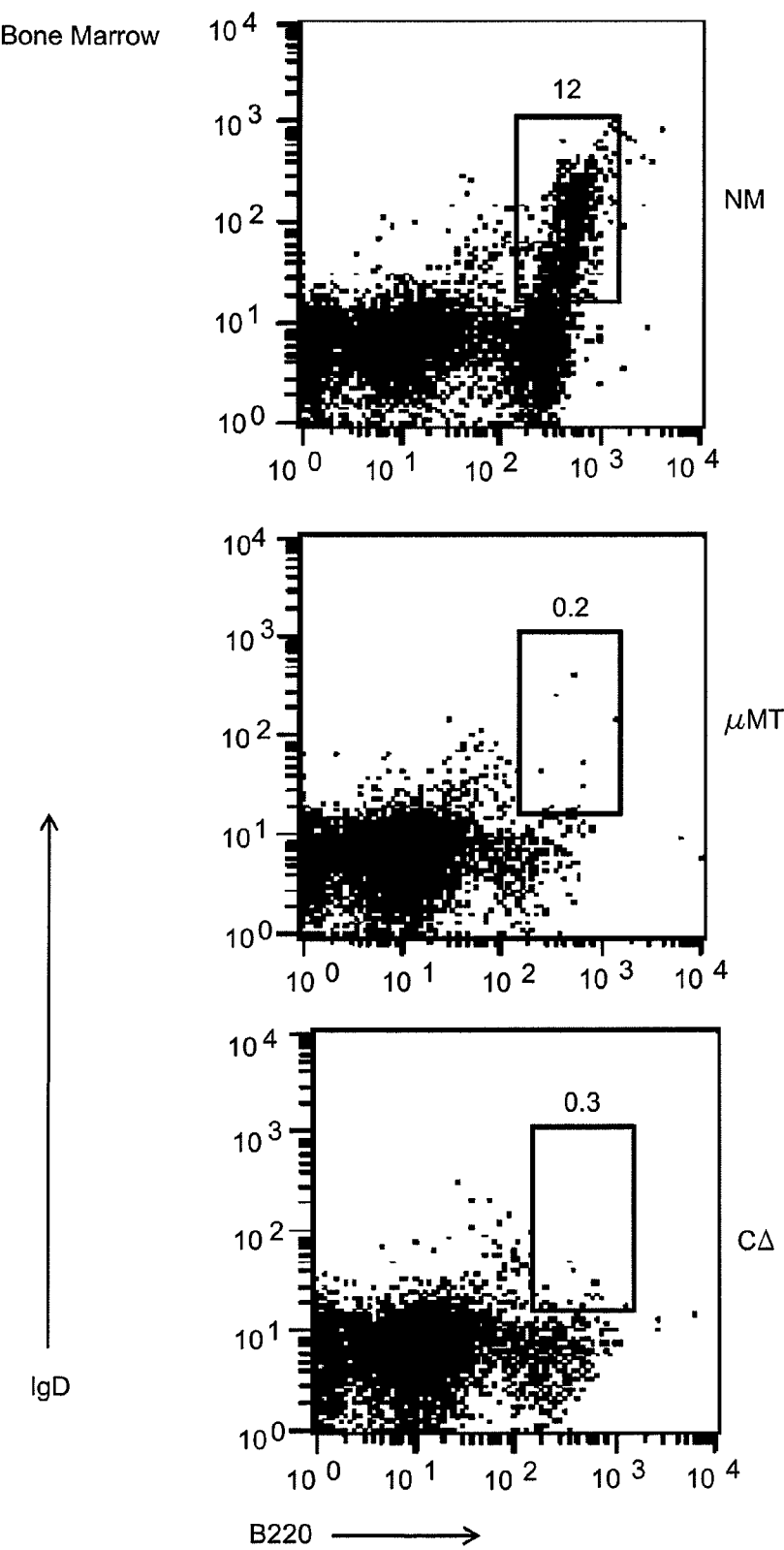
Figure 16F:
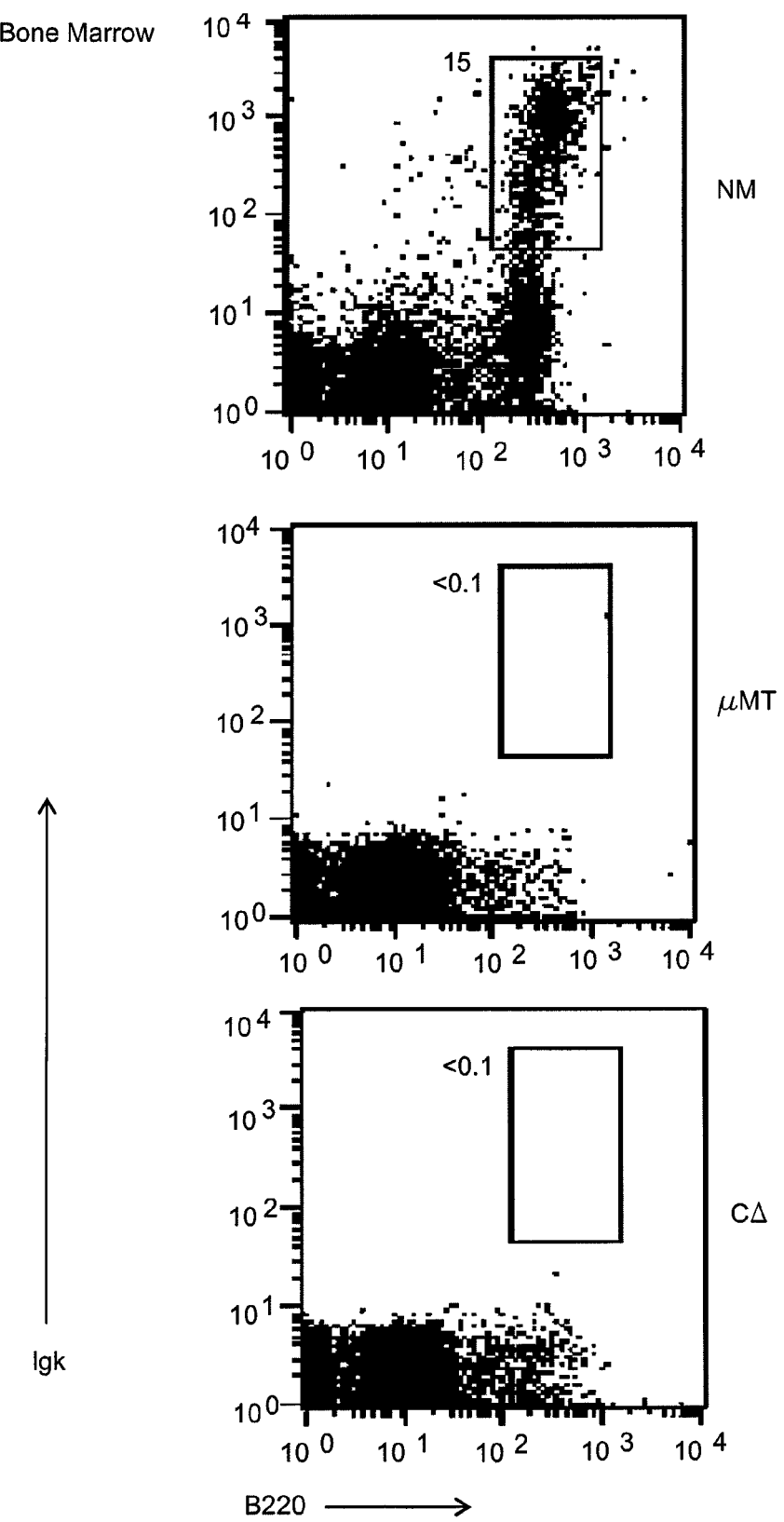
Figure 16G:
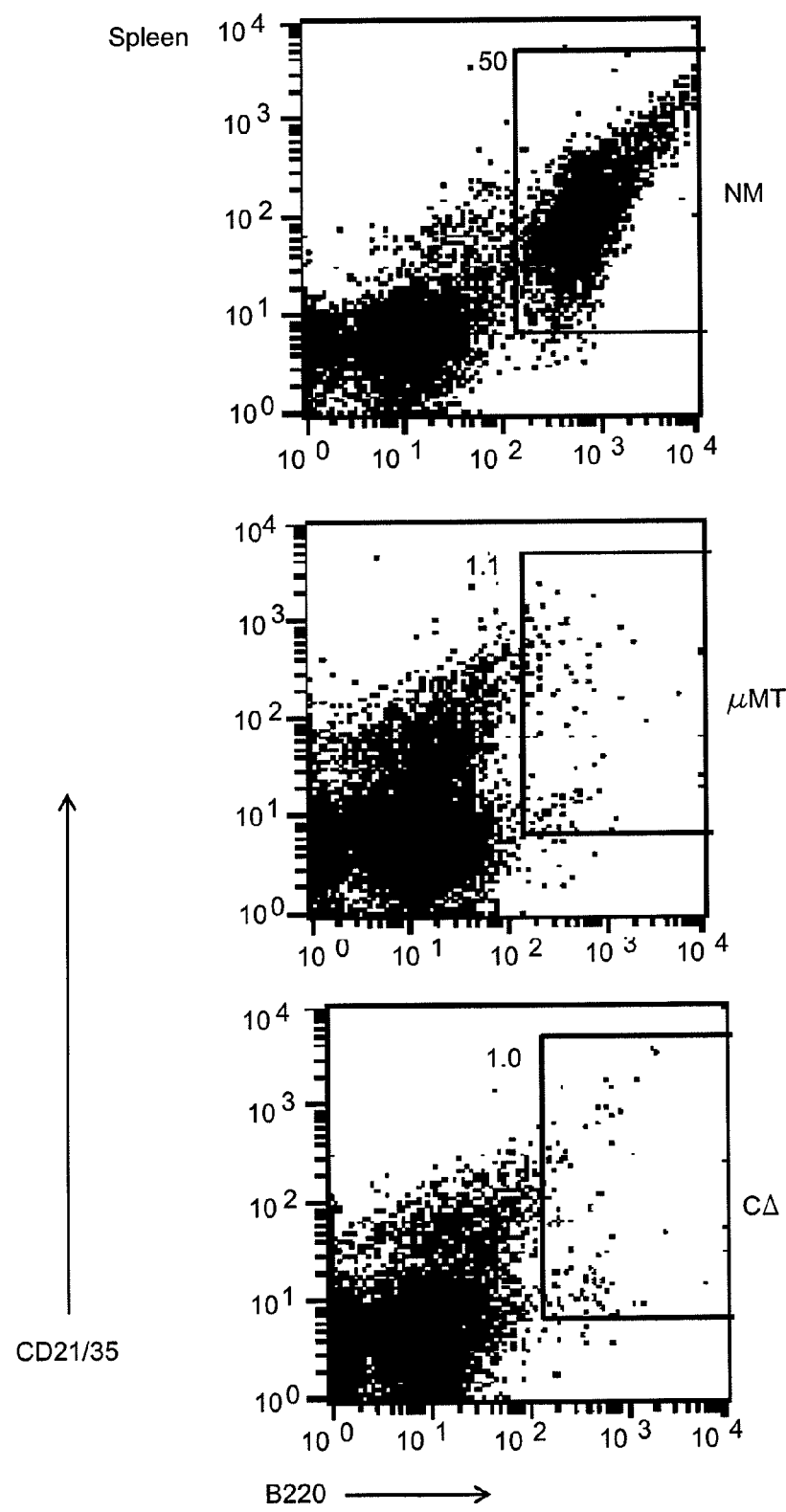
Figure 16H:
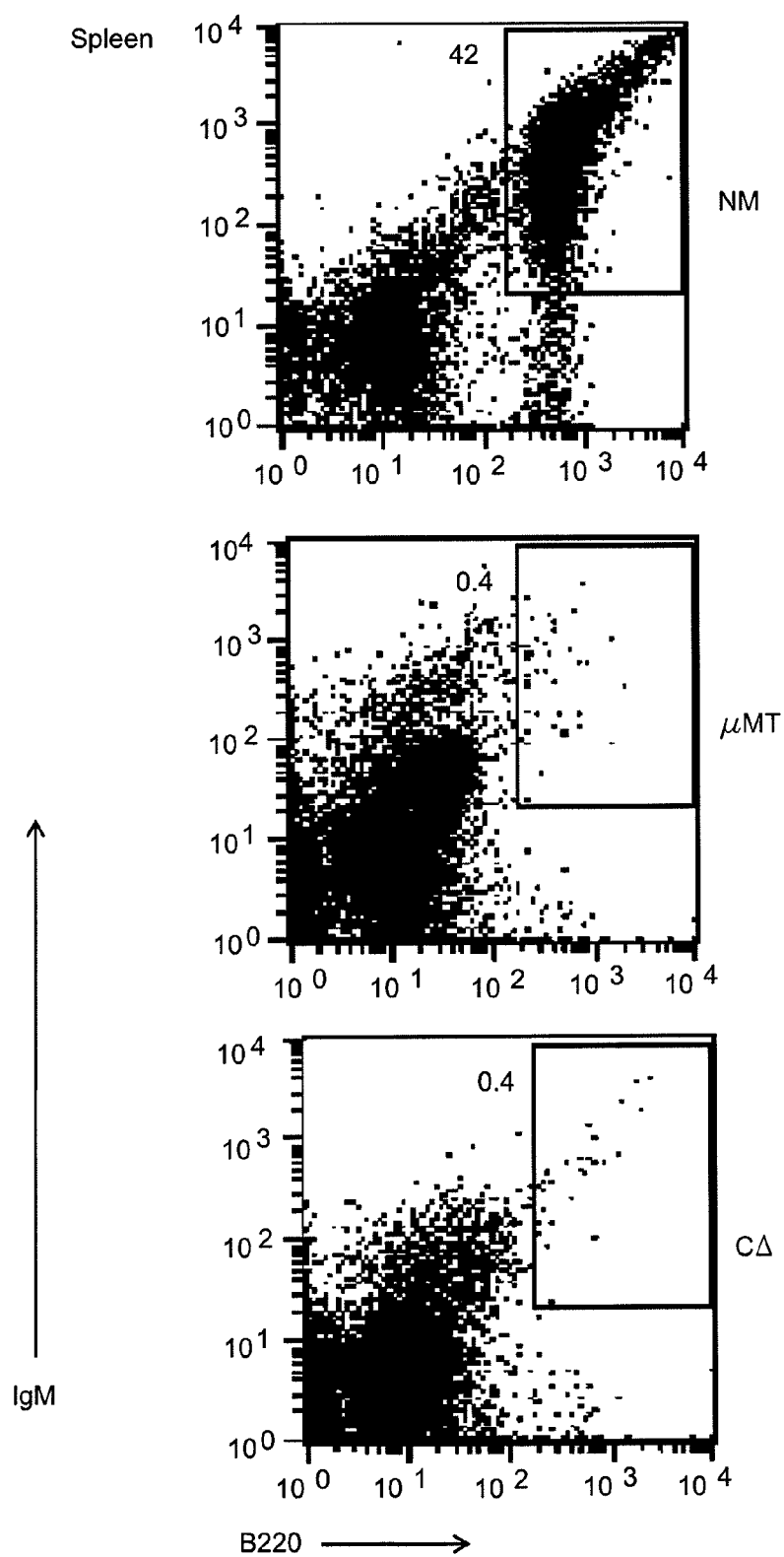
Figure 16I:
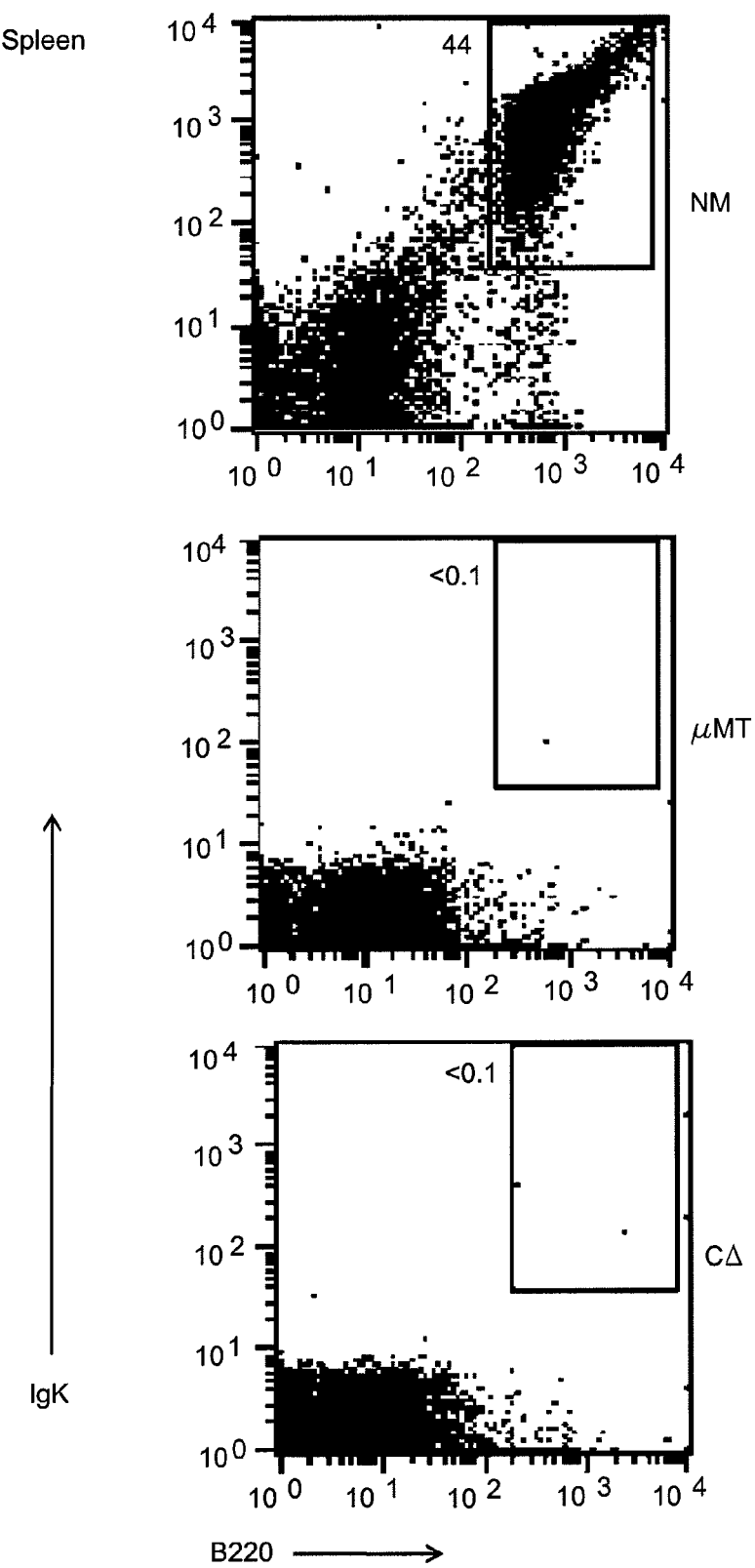

FIG. 15 shows the results of PCR analysis of first and second generation offspring obtained following crossing the two germline transmission mice carrying both targeting events, $\mu^{lox}$ and $3'E^{lox}$, with Cre$^+$ animals FIG. 16 shows the results of flow cytometry analysis of bone marrow and spleen cells from homozygous CΔ (IgHC deletion) mice.

Figure 17:
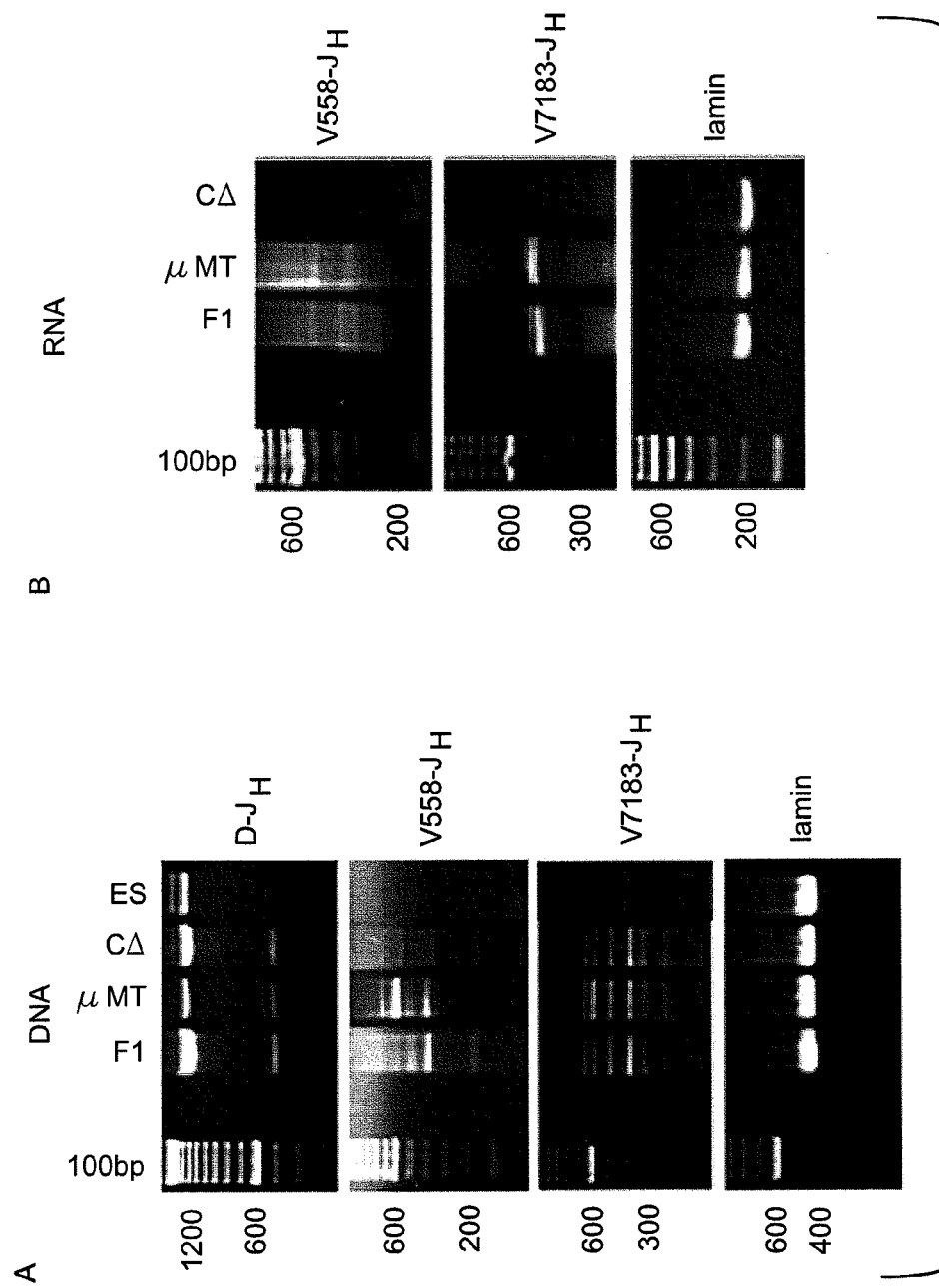

FIG. 17 shows (A) the results of analysis of D-J and V-D-J rearrangement by PCR, performed to test the engagement of the IgH locus in rearrangement of DNA from bone marrow cells, and (B) single-step RT-PCR transcriptional analyses of RNA prepared from bone marrow cells and single-step RT-PCR.

Figure 18:
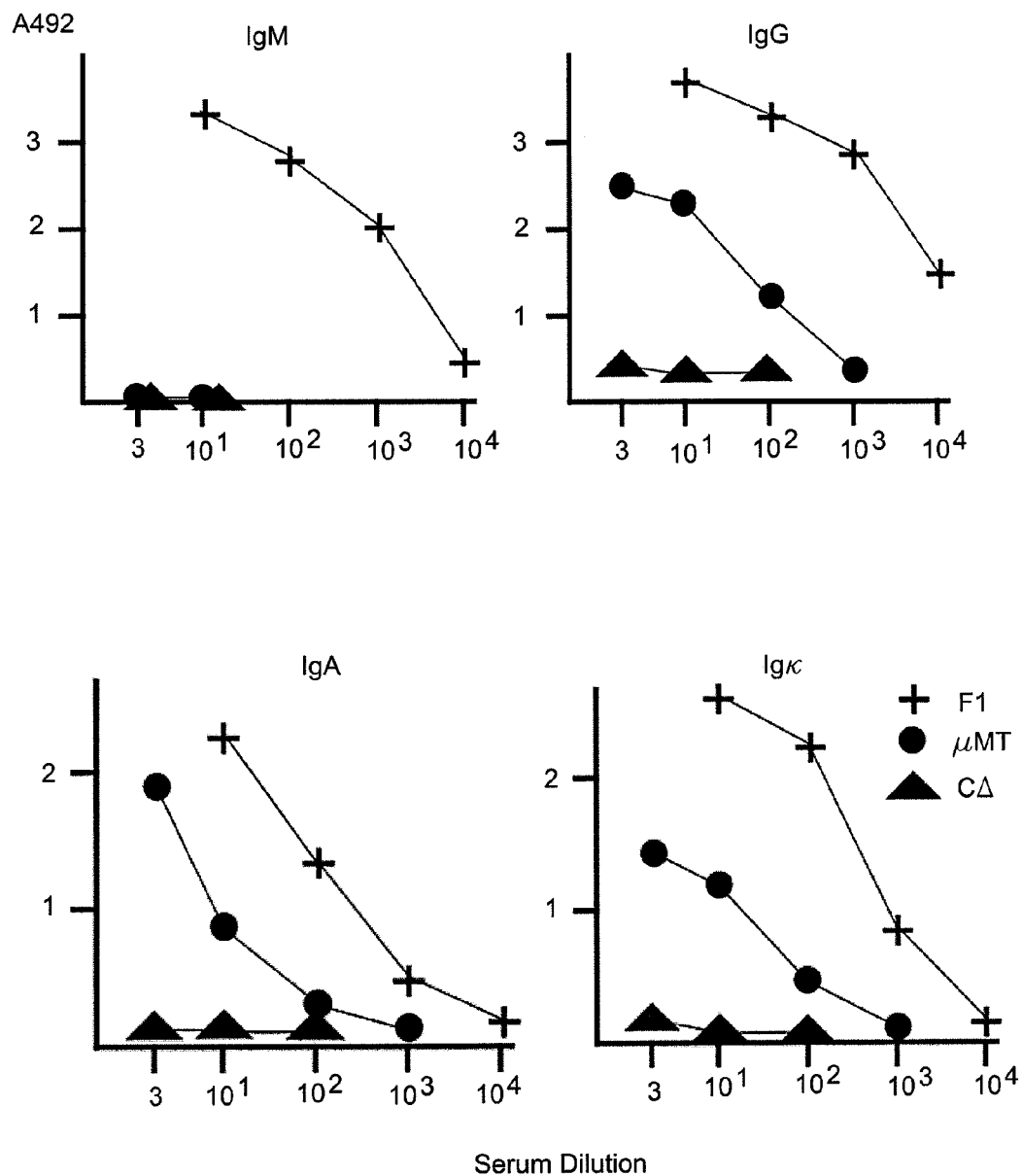

FIG. 18 shows the results from ELISA performed on serum from F1, CΔ and μMT mice; in the serum of CΔ mice, no presence of any Ig or individual fractions of IgM, IgG or IgA was found.

EXAMPLES

Example 1

Preparation of the Targeting Construct for the 5' Cμ Region

A λ phage library, obtained from E14 ES (embryonic stem) cell DNA (Sambrook, Frisch, Maniatis, Molecular Cloning, A laboratory manual, Cold Spring Harbor Laboratory Press, 1989), was hybridised with a 4.5 kb BamHI fragment comprising Cμ (Zou et al, Int. Immunol. 13, 1489-1499, 2001) several positive clones were identified and mapped. Hybridisation methods are well documented in the literature and known by researchers skilled in the art.

A loxP site was added to the puromycin gene (Tucker et al., Genes Dev., 10, 1008-1020, 1996) by PCR (forward primer oligo BamHI-loxP-puro: 5'TTTGGATCCATAACTTCG-TATAATGTATGCTATACGAAGTTATCGACCTCG AAATTCTACCGGG3' (SEQ ID NO: 1) and reverse primer oligo BclI-puro: 5' TTTGATCAGCTGATCTCGTTCT-TCAGGC 3' (SEQ ID NO: 2) which allowed the retrieval of loxP-puro on a BamHI-BclI fragment).

Figure 6:
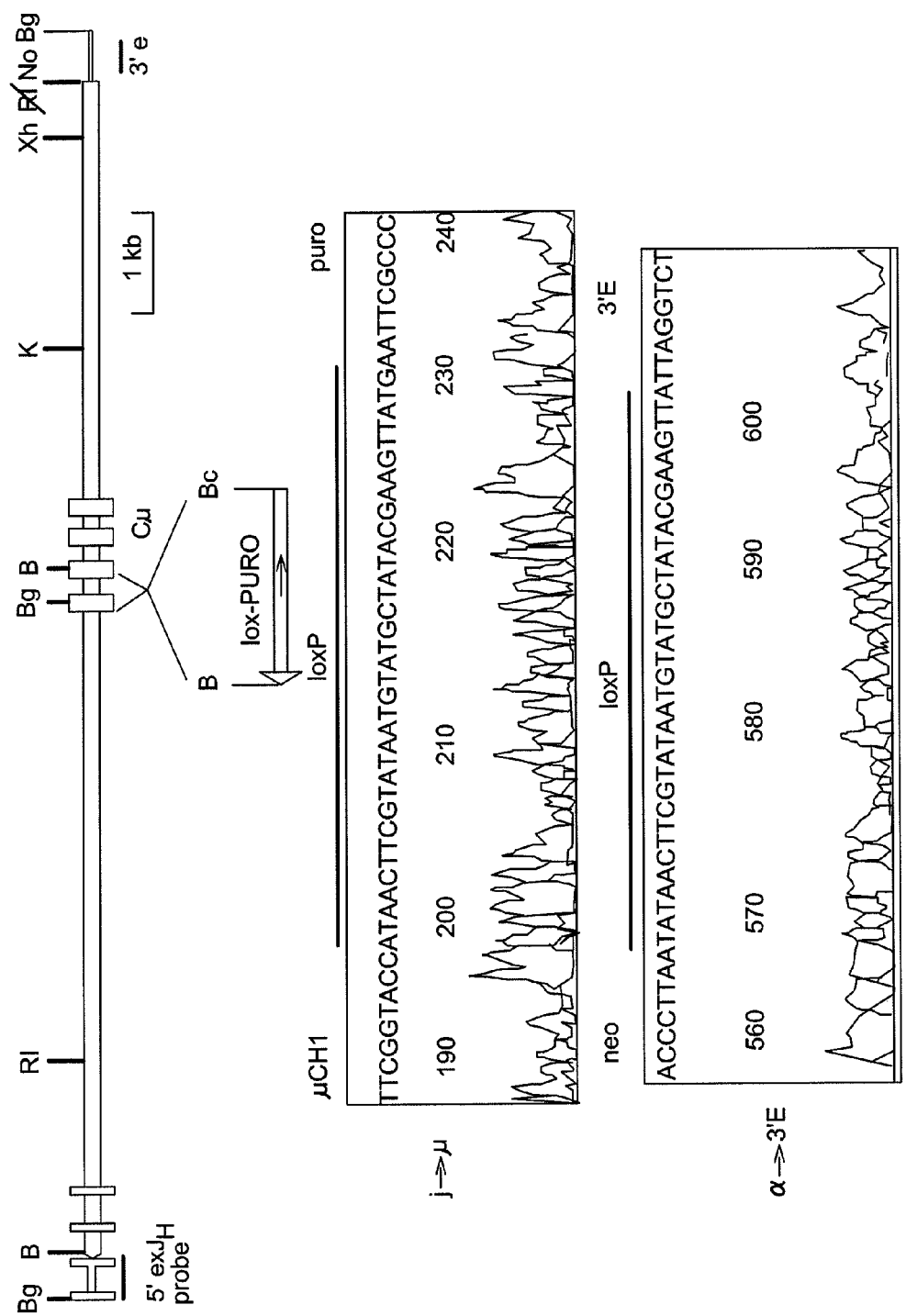
FIG. 6 illustrates the Cμ targeting construct and the sequence analysis of loxP in the 2 targeting constructs, which verified their correct orientation to allow Cre mediated deletional removal of all C genes. Sequences correspond, from top to bottom, to SEQ ID NO: 22 and SEQ ID NO: 23, respectively.

The ~6.5 kb fragment from JH3/4 to Cμ1 and the ~5.5 kb fragment from Cμ2 to Cδ were linked with a loxP-puromycin resistance gene on a ~2 kb BamHI-BclI fragment (see FIG. 6).

The targeting construct for Cμ ($\mu^{lox}$) was assembled by subcloning of BamHI-BglII fragments into pUC19 (Invitrogen). The 3' EcoRI site was replaced by NotI using partial digest and blunt end linker insertion. In the resulting 5' targeting construct for Cμ, a loxP sequence was inserted upstream of a selectable marker gene (puromycin) which was inserted at the Cμ gene.

Example 2

Preparation of the Targeting Construct for the α3' Region

The λ phage library (see above), obtained from E14 ES (embryonic stem) cell DNA was hybridised with a 3.5 kb BglII fragment comprising the rat α 3'enhancer (Pettersson et al, Nature, 344, 165-168, 1990) and several positive clones were identified and mapped.

Figure 2:
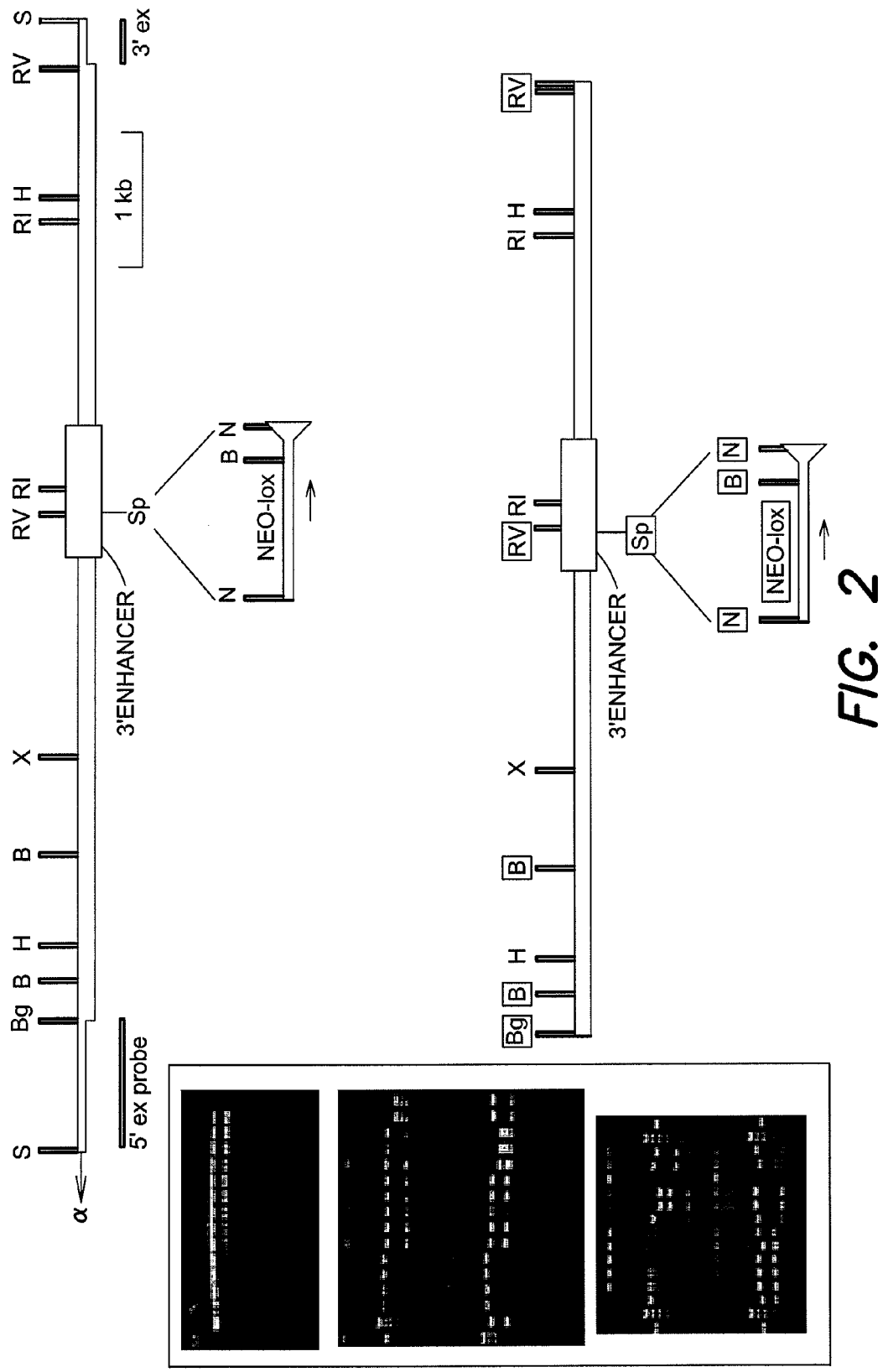
FIG. 2 illustrates the targeting construct for the 3' region, restriction digests confirming correct assembly are provided on the left hand side.

The α3'enhancer region on a ~9 kb SacI fragment was cloned into pUC19 and the internal EcoRV site was changed to SpeI by partial digest and blunt end linker insertion. This unique site allowed the integration of a ~1.3 kb Neomycin-loxP gene on a compatible NheI fragment (see FIG. 2). A loxP site was added to the neomycin resistance gene (Stratagene, La Jolla, Calif.) by blunt end insertion of loxP from pGEM-30 (Gu, H., Y.-R. Zou, and K. Rajewsky. Cell, 73, 1155-1164, 1993) and by oligonucleotide insertion (Sauer, Mol. Cell. Biol., 7, 2087-2096, 1987) in the α3' targeting construct ($3'E^{lox}$) downstream of the neomycin gene.

Example 3

Confirming Orientation of the loxP Sites

Correct orientation of the loxP site in each targeting construct was verified by DNA sequencing (see FIG. 6). The loxP sites must be in the same linear orientation to each other so that upon targeted insertion of both loxP sites Cre-mediated deletional removal can be obtained. Here, this allows the removal of both inserted selectable marker genes and the region between Cμ and the 3'α enhancer at the end of the C gene cluster.

Example 4

Preparation of ES Cells

ZX3 ES cells, obtained from the 129 sv mouse strain were produced using methods described by Hogan, B., R. Beddington, F. Costantini, and E. Lacy. 1994 in Manipulating the mouse embryo, a laboratory manual. Cold Spring Harbor Laboratory Press. ZX3 is an in house designation for these murine embryonic stem cells derived by Zou Xiangang upon his 3$^{rd}$ attempt.

Example 5

ES Cell Transfection and Southern Hybridisation

Figure 3:
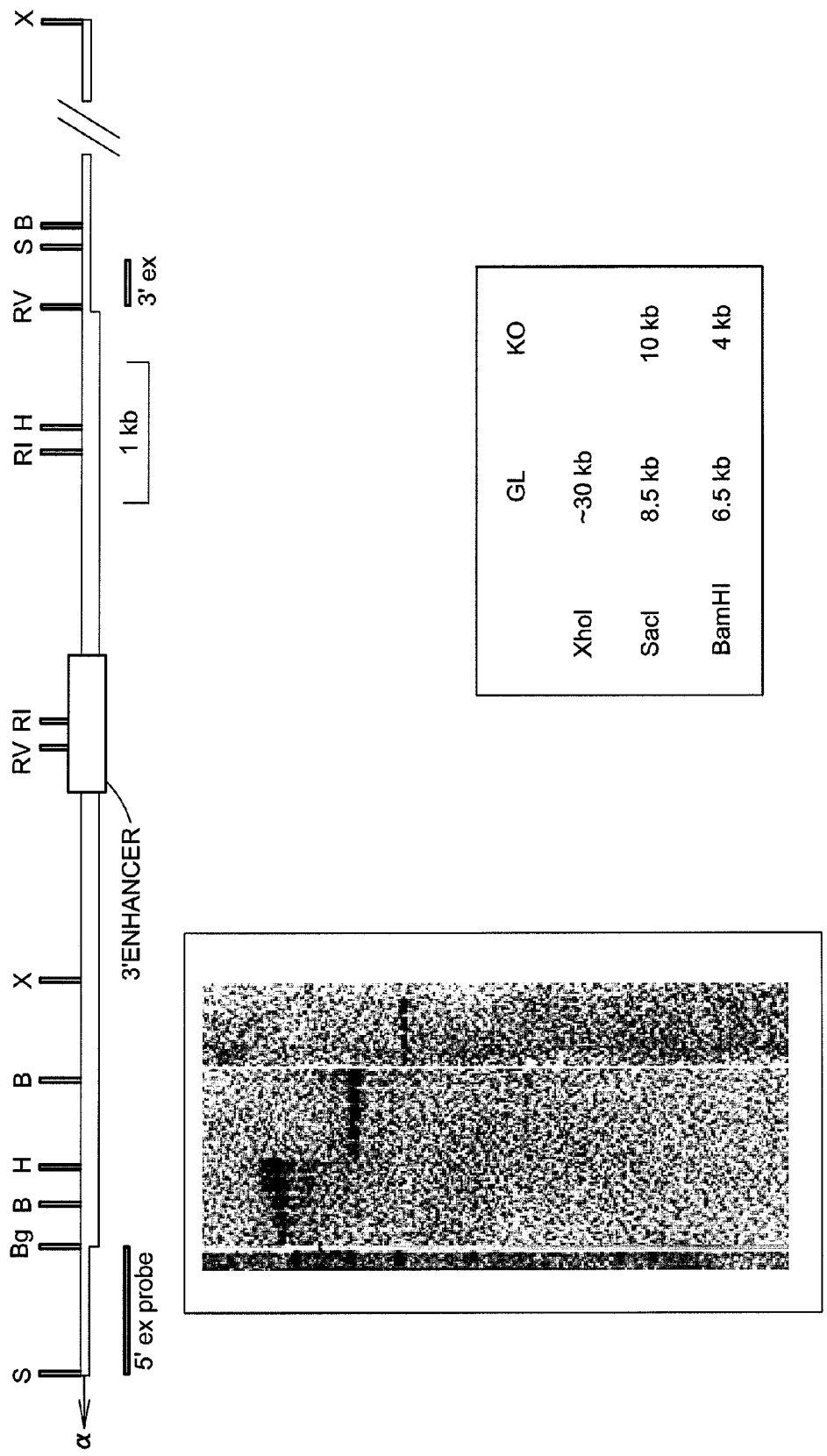
FIG. 3 illustrates a test Southern blot showing the germline (GL) fragments when hybridising with the 3' ext(ernal) probe indicated. Samples with homologous integration or knock-out (KO) produce an additional ~10 kb SacI and ~4 kb BamHI band in addition to a weaker germline band for the unmodified allele.

The Cμ targeting construct was linearised using BamHI and NotI and the α3'enhancer targeting construct was linearised with BglII and EcoRV (see FIG. 3). For each construct separately, about 10 μg purified fragment (purification kit #28304, Qiagen, Crawley, West Sussex, UK) was mixed with ~10$^7$ ZX3 ES cells, obtained from the 129 sv mouse strain, and subjected to electroporation and selection as described (Zou et al, Eur. J. Immunol., 25, 2154-2162, 1995; Zou et al, Int. Immunol. 13, 1489-1499, 2001). DNA from G418 resistant (Neo$^r$) clones for the α3'enhancer construct was prepared and analysed in Southern blots as described (Sambrook, Fritsch, Maniatis, Molecular Cloning, A Laboratory Manual, Cold Spring Harbor Laboratory Press, 1989). This allowed the identification of one correctly targeted clone (355) to be used for introduction of the Cμ construct and puromycin selection which resulted in one correctly targeted clone (212) identified with correct insertion into Cµ and the 3'α enhancer.

Hybridisation probes were a ~0.4 kb 3' external EcoRV-SacI fragment for the α3'enhancer (see FIG. 5) and 5' and 3' external probes for Cµ described in Zou et al., Int. Immunol. 13, 1489-1499, 2001 (see FIGS. 9 and 10). These were the 5' external probe, a ~0.5 kb BamHI-BglII fragment, and a 335 bp 3' external probe, obtained by PCR using plasmid DNA with the following oligonucleotides: forward primer 5'AACCTGACATGTTCCTCC3' (SEQ ID NO: 3) and reverse primer 5'GGGATTAGCTGAGTGTGG3' (SEQ ID NO: 4). PCR conditions were 95° C. 1 min, 58° C. 1 min and 72° C. 30 sec for 30 cycles.

Figure 4:
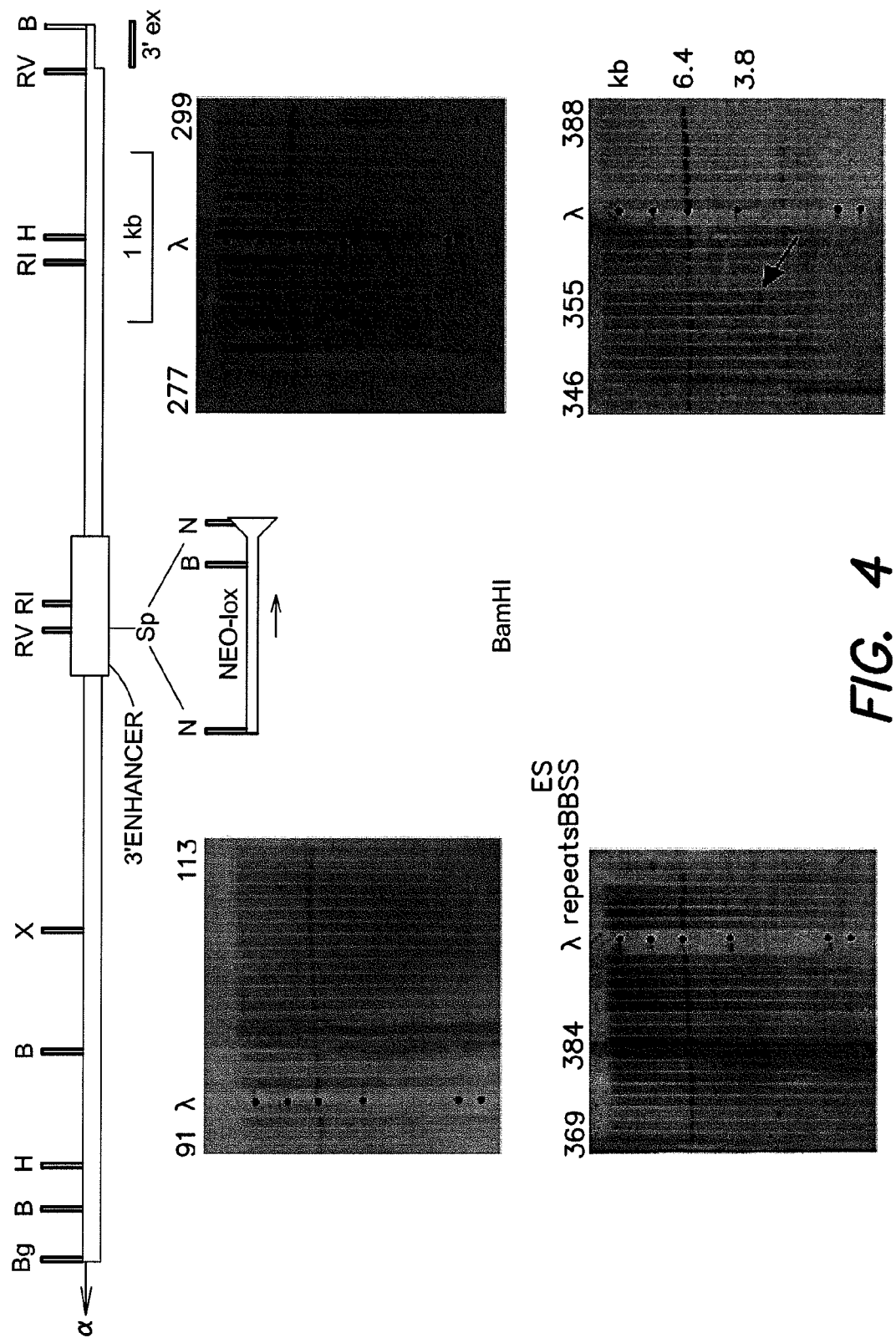
FIGS. 4 and 5 illustrate that following transfection of ZX3 (ZX3 is an in house designation for murine embryonic stem cells produced using methods described by Hogan, B., R. Beddington, F. Costantini, and E. Lacy. 1994 in Manipulating the mouse embryo, a laboratory manual. Cold Spring Harbor Laboratory Press), embryonic stem cells were selected and screened and from 601 ES cell clones, one targeting event, clone no. 355, was identified. Further Southern blot analysis of clone 355 is shown in FIG. 5 left hand side.
Figure 5:
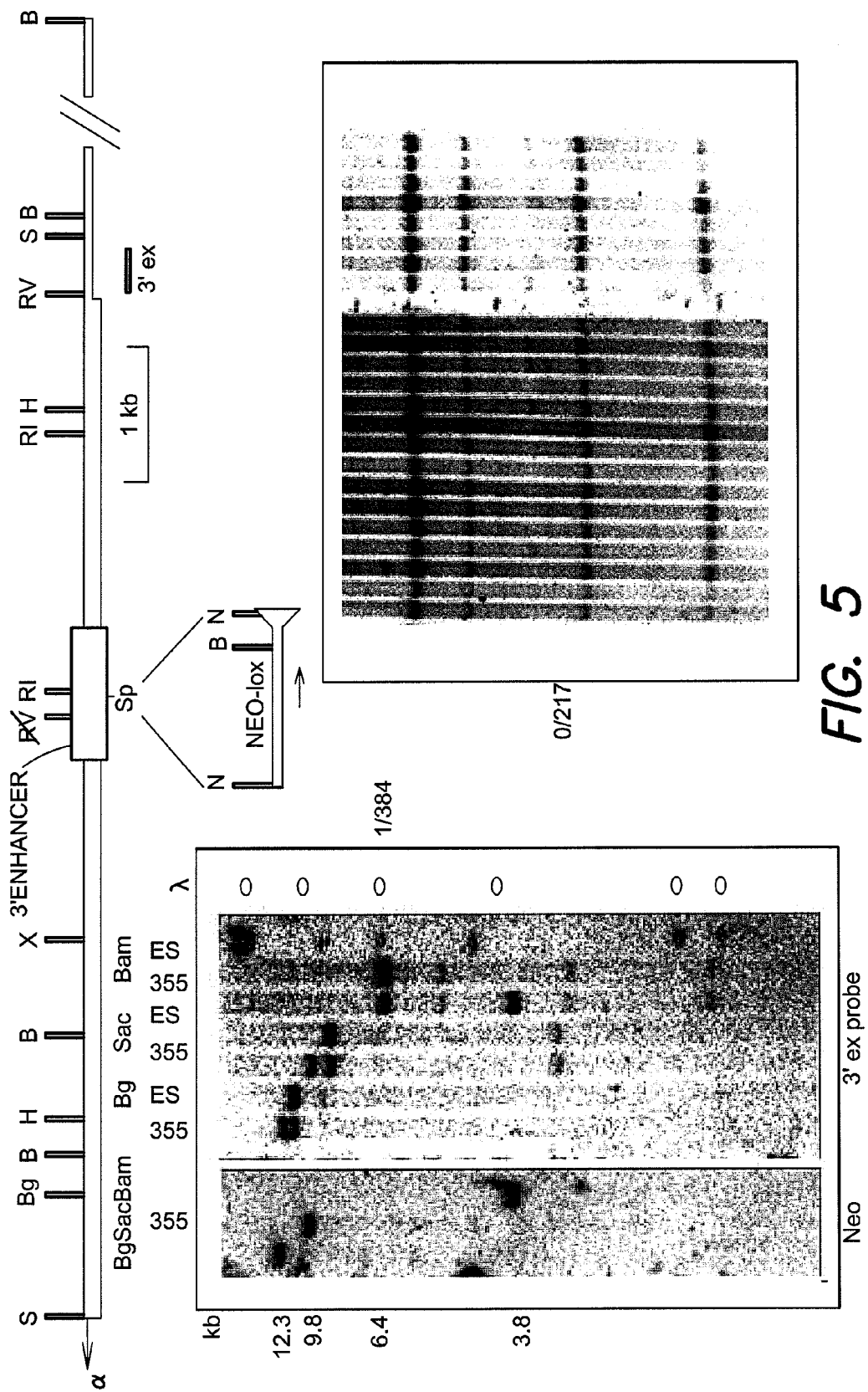

Southern blots were carried out as above with the results given in FIGS. 3, 4 and 5 which shows the germline (GL) fragments when hybridising with the 3' ext(ernal) probe indicated. Samples with homologous integration or knock-out (KO) produced an additional ~10 kb SacI and ~4 kb (3.8 kb) BamHI band in addition to a weaker germline band for the unmodified allele.

Figure 9:
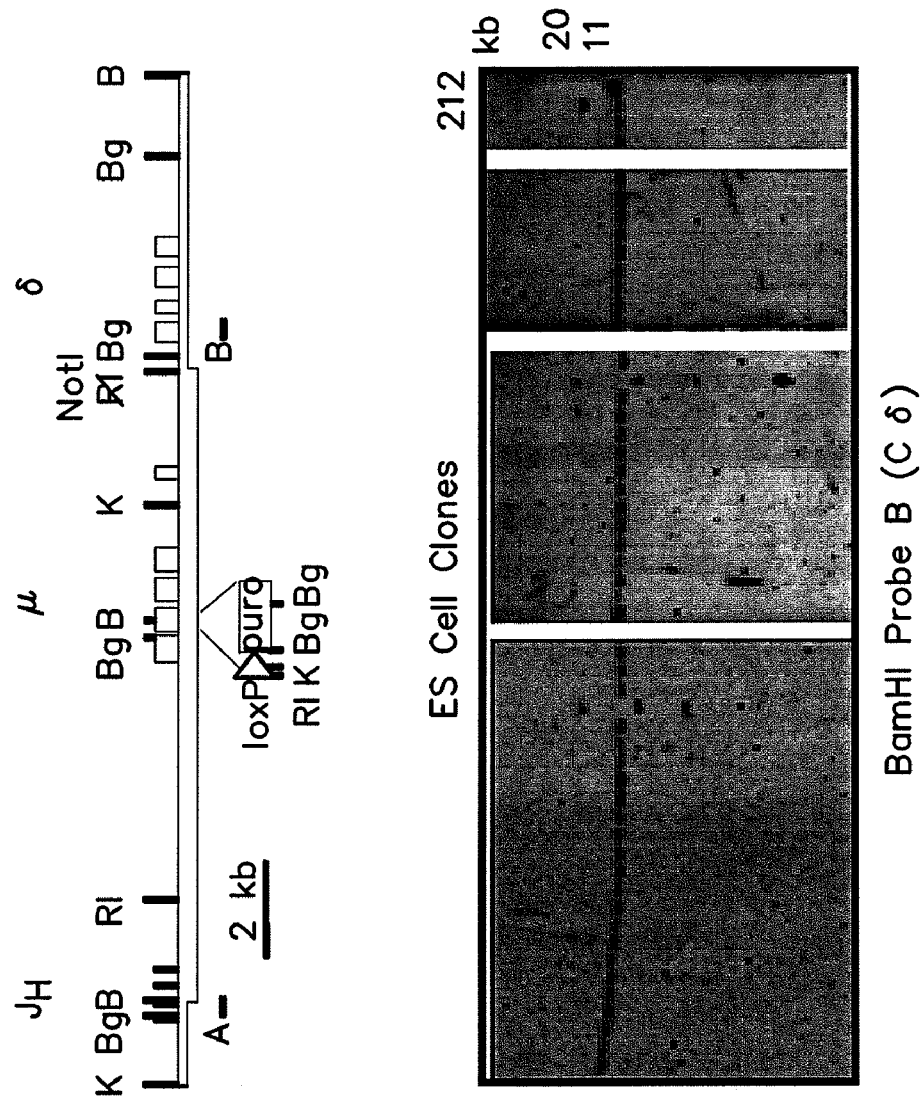
FIG. 9 shows the 355 ES cell clone that was used for further targeting with the Cμ targeting vector. External probes are indicated as A and B. This resulted in one dual targeting event, clone 212.

FIG. 9 shows results from ES cell clone 355 which was used for further integration of the Cµ targeting vector. Southern blot analysis was carried out using probe B and probe A (not shown) which identified one double targeting event, clone 212.

For Cre-mediated deletion in transient transfection 10 µg of supercoiled plasmid pBS185 (Gibco, Cat. No. 10347-011) was mixed with $10^7$ ES cells in 0.8 ml ES cell medium and kept at RT for 10 min. After transfer into a 0.4 cm electrode gap cuvette (Bio-Rad, 65-2088) electric pulses were applied twice at 230V and 500 µF. Cells were cultured at 37° C. for 30 min and then transferred at low density into 6-well plates containing feeder cells. After 8 to 10 days in culture clones were picked and equally split in order to test their survival in selective medium. About 10% of the clones perished and in their separate fractions deletion was identified by PCR and Southern analysis.

Figure 10:
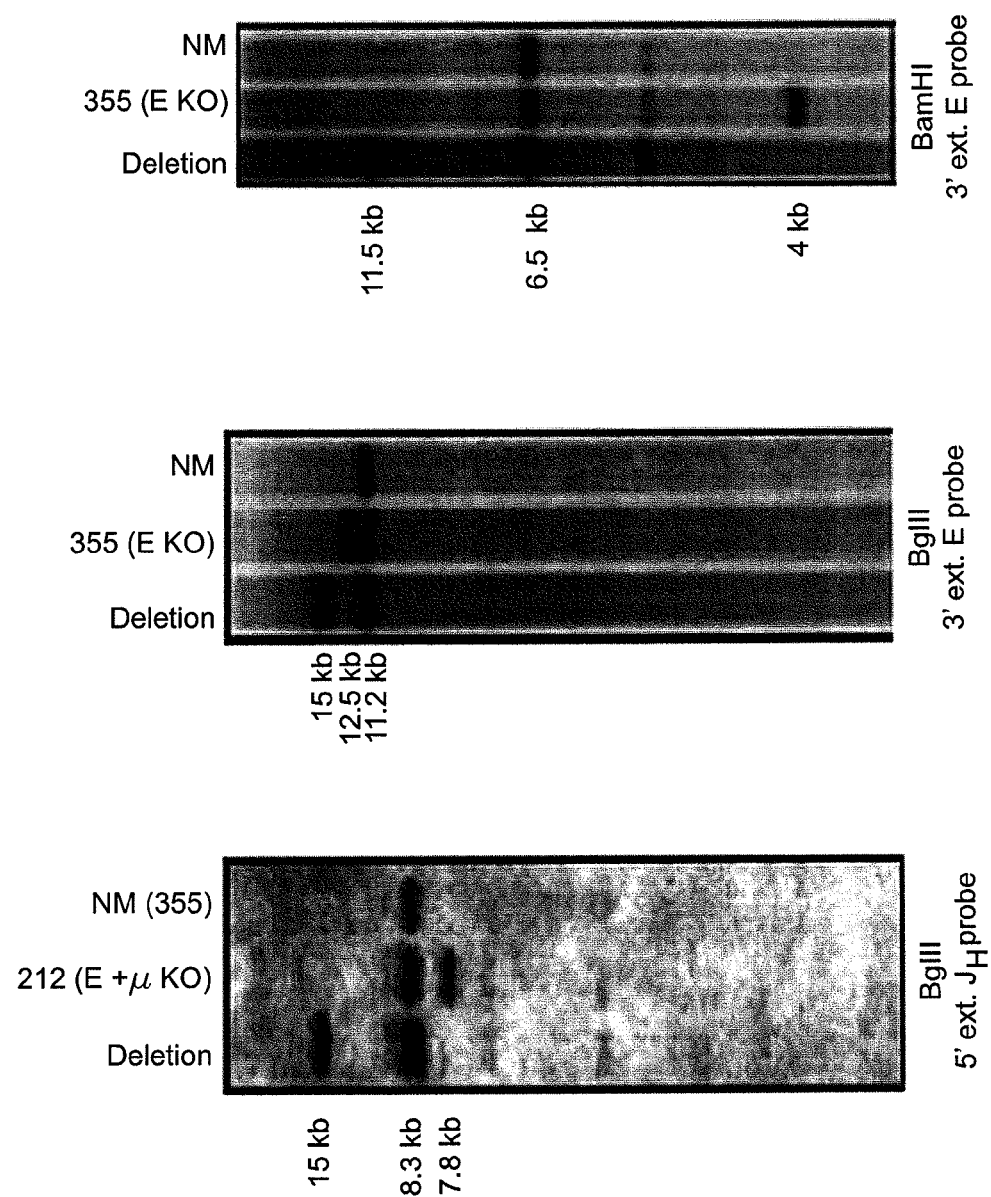
FIG. 10 shows how integration was verified. Clone 212 carries two targeted integrations, upstream and downstream of the C gene cluster. Transfection of the ES cells with a Cre vector allowed deletion analysis and suggested that both targeting events were on one allele.

FIG. 10 shows how integration was verified by Southern blot analysis as described above. Clone 212 carries two targeted integrations, upstream and downstream of the C gene cluster. Transfection of the ES cells with the Cre vector allowed deletion which increased the resulting hybridisation band as expected.

Figure 7:
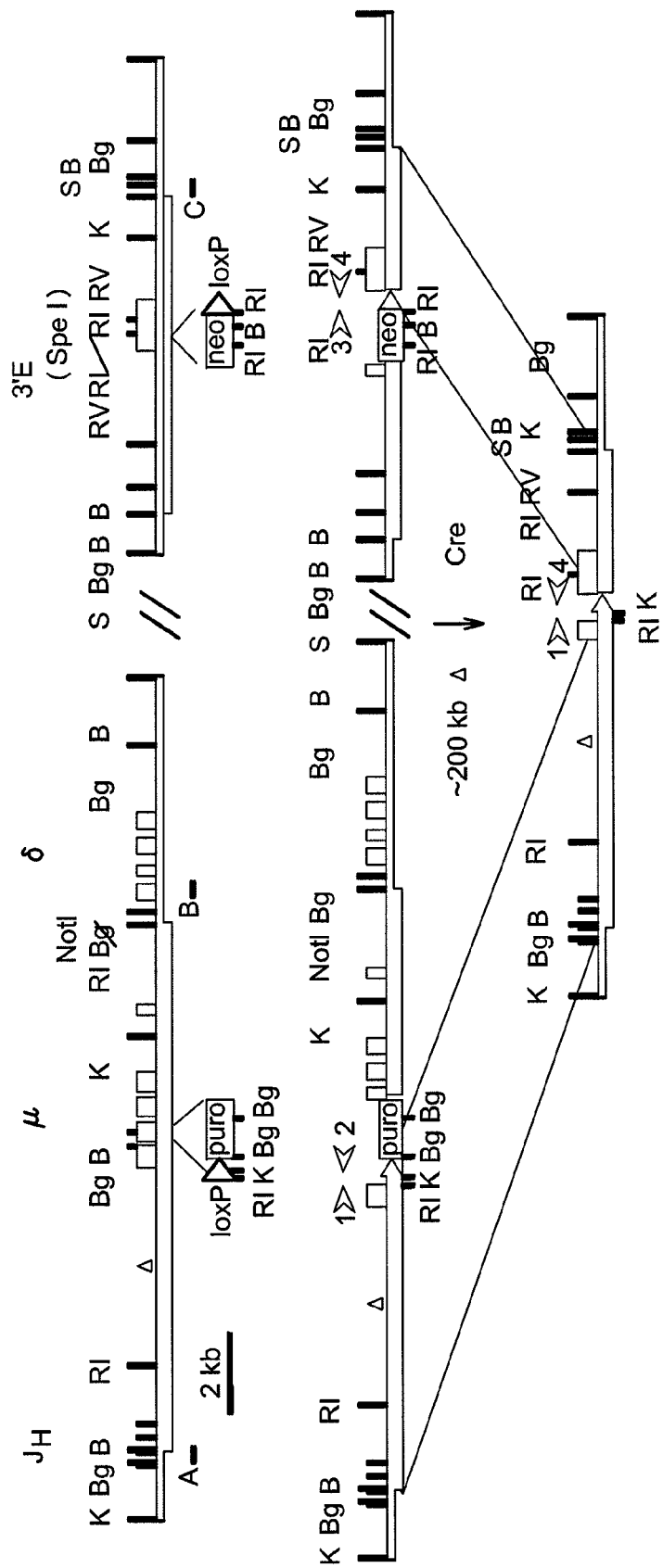
FIG. 7 shows the scheme for targeted integration and deletion of the C gene cluster.

The removal of all 8 C-region genes on a ~200 kb region involved targeted integration of loxP-flanked homology constructs ($\mu^{lox}$ and 3'$E^{lox}$) into Cµ exons 1 and 2, with the removal of a 330 bp BglII-BamHI fragment, and into the 3' enhancer, located ~15 kb downstream of Cα (FIG. 7). Homologous integration was identified by Southern hybridisation using external probes (FIG. 10). This produced in a BglII digest and hybridisation with the 5'$J_H$ probe an 8.3 kb germline and a 7.8 kb targeting band, whilst the 3'E probe identified an 11.2 kb germline and a 12.5 kb targeting band. Using the 3'E probe in a BamHI digest identified a 6.5 kb germline and a 4 kb targeting band. To assess the efficiency of Cre-loxP-mediated C-gene removal Cre plasmid pBS185 was transfected and transiently expressed in double-targeted ES cells. Upon C-gene deletion a 15 kb BglII fragment was obtained when hybridising with the 5'$J_H$ and, separately, with the 3'E probe and in a BamHI digest an 11.5 kb fragment was obtained with the 3'E probe. These findings agreed with the map of the locus. Analysis of individual colonies by Southern blotting and PCR, with examples given in FIG. 10, showed locus deletion in about 10% of the clones. This agreed well with the initial assessment of cellular up-take and expression of the Cre-gene which was verified by transferring part of each colony into selective medium where about 1 in 10 clones died. The double targeted ES cell clone 212 was used to derive mice as in vitro deletion was easily obtained which suggested that both modifications integrated on the same allele and that in vivo deletion could possibly be achieved by breeding of germline transmission mice with Cre expressers [15].

Figure 11:
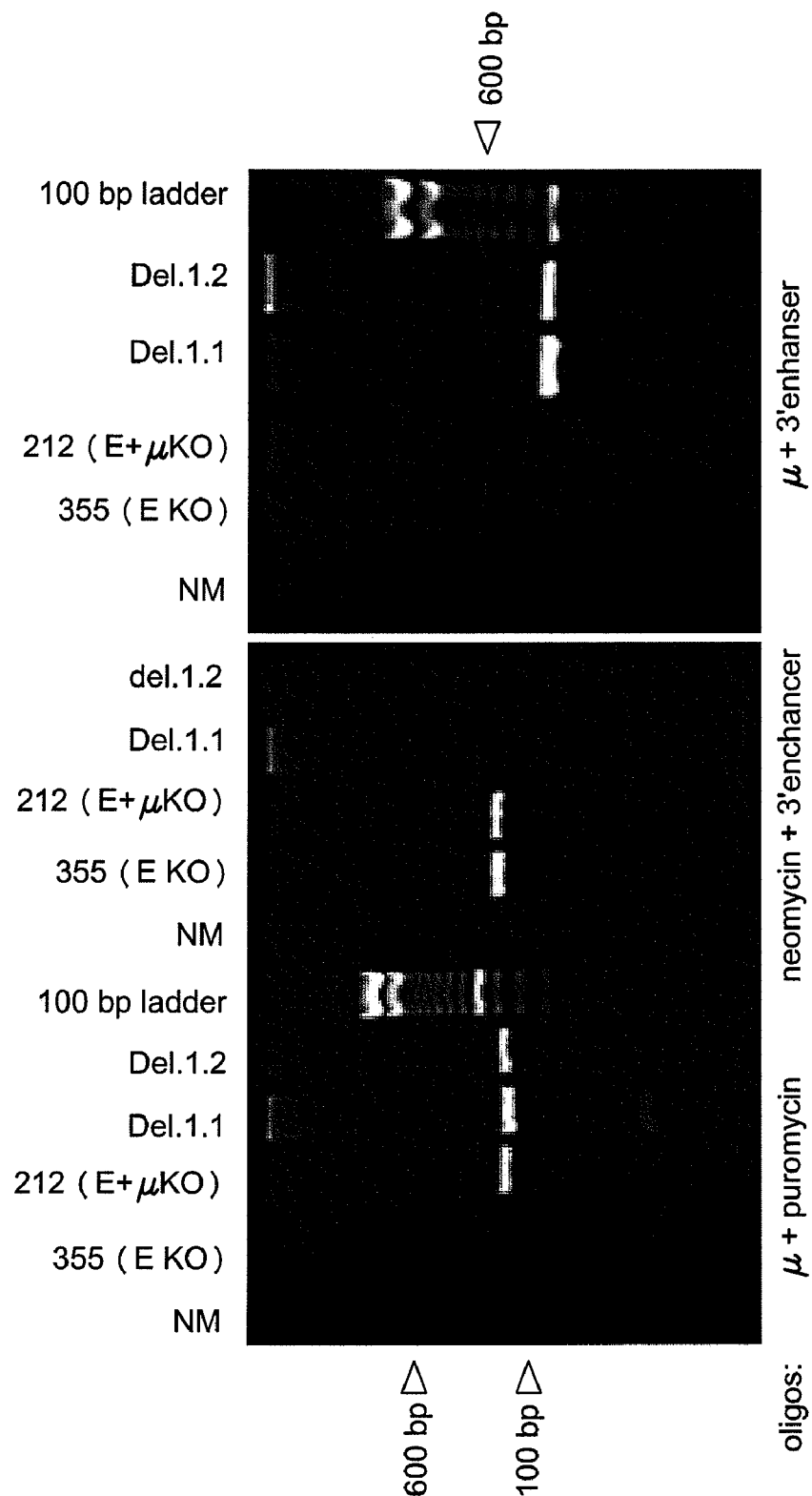
FIG. 11 shows that clones after Cre transfection appear to produce a PCR band using primers 1 and 4 illustrated in FIG. 7. However, one band indicating targeted integration, primers 1 and 2, remained. This may indicate mixed clones or that the Cre-loxP mediated removal is not achieved in all cells of the clones.

Verification of the two targeted integration events upstream (5' Cµ) and downstream (α3') of the C gene cluster was confirmed in clone 212 by transient transfection of the ES cells with the Cre vector and deletion analysis by PCR using primer pair 1-4 (see FIGS. 7 and 14, for P1 and P4 see Examples) which showed deletion of the C gene cluster and suggested that targeted integration of the two constructs happened on one allele (see FIG. 11).

FIG. 11 shows that clones after Cre transfection appear to produce a PCR band using primers 1 and 4 illustrated in FIGS. 7 and 14, and in Example 8. However, one band indicating targeted integration, primers 1 and 2, remained. This may indicate mixed clones or that the Cre-loxP mediated removal is not achieved in all cells of the clone. Note, as this is not seen in Southern blot hybridisations, FIG. 10, is it likely to represent low level contamination picked up by very efficient PCR amplification.

Example 6

Generation of Mice and Breeding

ES cell clones with targeting events (355 for the single α3'enhancer targeting event, integration of 3'$E^{lox}$ into the α3' enhancer, and 212 for the α3' enhancer (3'$E^{lox}$) and 5' Cµ ($\mu^{lox}$) targeting events) were injected into BALB/c blastocysts, transplanted into (C57BL/6×CBA)F1 foster mothers and chimaeric mice and germline transmission was obtained as described (Hogan, B., R. Beddington, F. Costantini, and E. Lacy. 1994. Manipulating the mouse embryo, a laboratory manual. Cold Spring Harbor Laboratory Press). The mice were further analysed by PCR as described below and were derived, bred and investigated in accordance with UK Home Office project licence regulations.

Crossing animals carrying both targeting events with Cre mice (for methods see reference 15, Zou et al (2003)) resulted in locus deletion.

Example 7

Southern Blot Analysis of Germline Transmission Mice Derived from ES Clone 355

Figure 8:
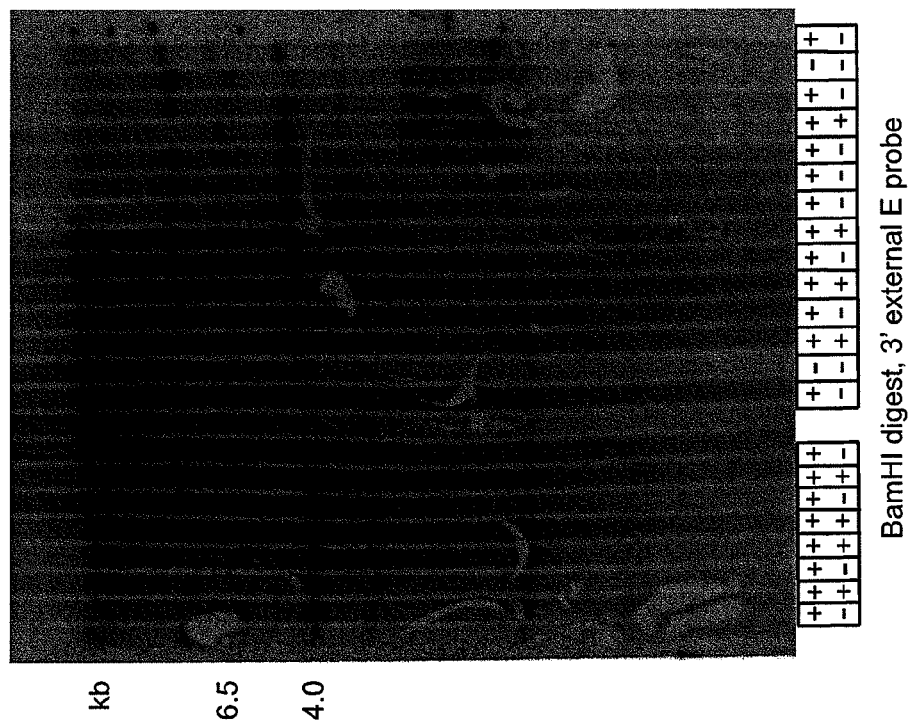
FIG. 8 shows Southern blot analysis of potential 355 (3'E) homozygous derived from ES clone 355 and their crossing to homozygosity. The ~4 kb band indicates the targeting event, the ~6.5 kb band is the germline band and ++ indicates targeted integration on both alleles.

Southern blot analysis of germline transmission mice derived from ES clone 355 with the mice derived therefrom crossed to homozygosity was carried out using the 3' external E probe (C in FIG. 7). The ~4 kb band indicates the targeting event, the ~6.5 kb band is the germline band and ++ indicates targeted integration on both alleles. The results of the Southern blot are provided in FIG. 8.

For the derivation of transgenic mice expressing Cre-protein ubiquitously, the Cre plasmid pBS185 (GibcoBRL, Life Technologies, Paisley, UK) was linearised with ScaI and purified using a DNA purification kit (#28304, Qiagen, Crawley, West Sussex, UK). DNA was microinjected into the male pronucleus of F1 embryos (CBA×C57B1/6) according to standard methods (Hogan, see above) and several founders were produced, two of which showed a high gene/locus deletion rate when crossed with loxP mice.

Figure 12:
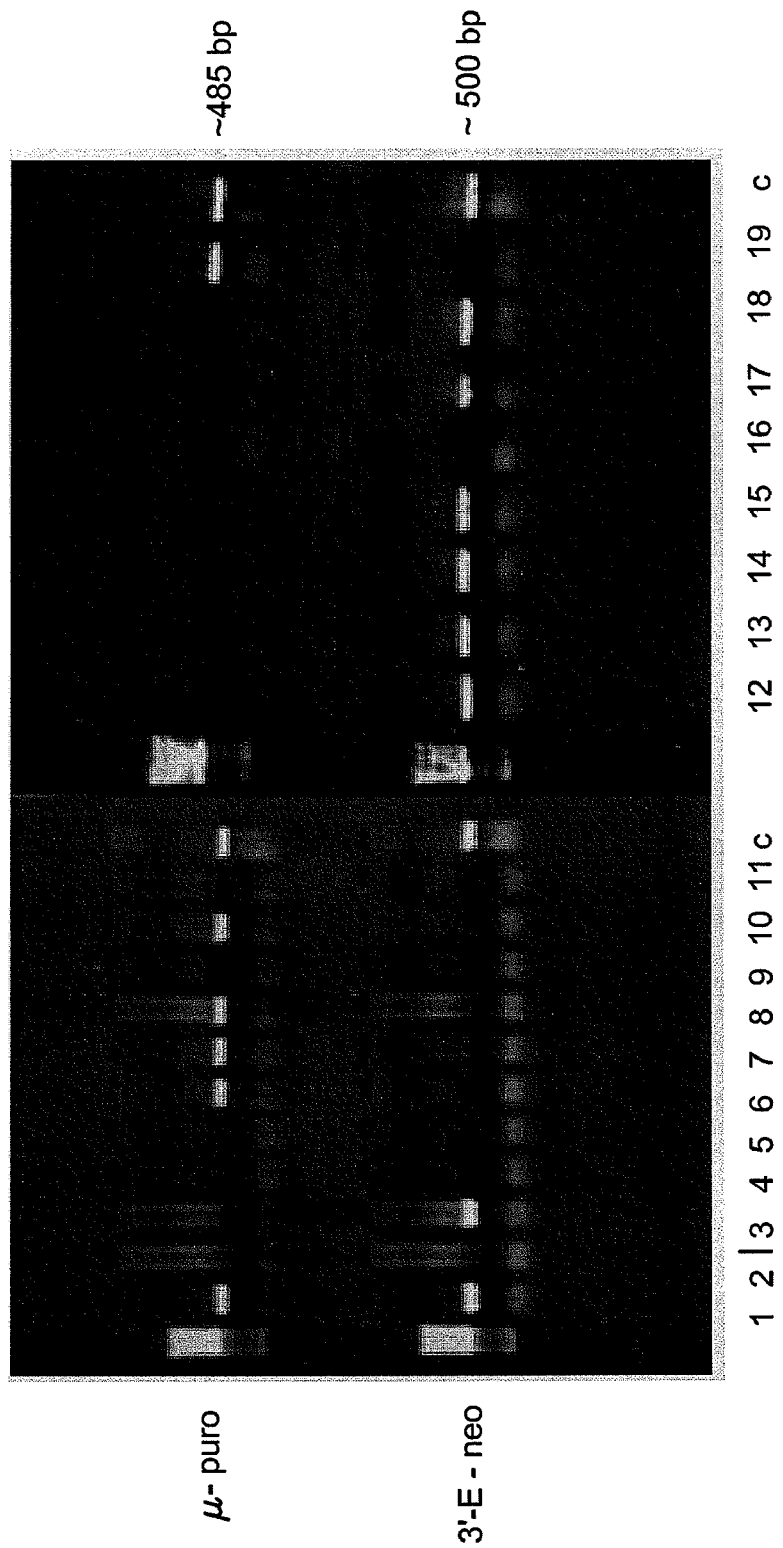
FIG. 12 shows PCR analysis of potential germline transmission mice (selected by coat colour) for both targeted integrations 3'E and μ. Unexpectedly, about half the number of germline transmission mice had an allele carrying either the 5' or 3' targeting event, but not both events. Of 19 mice, 6 were negative, 7 positive for targeted integration in 3'E, 5 positive for targeted integration in μ and one was positive for both targeting events. As germline transmission was about 50%

FIG. 12 shows that, unexpectedly, about half the number of germline transmission mice obtained from clone 212 had one allele carrying either the 5' or 3' targeting event, but not both events. As germline transmission was about 50% (half of the mice with the correct coat colour did not have the site-specific modification) it seems that the two targeted integrations are on one allele but that cross-over frequently separated the two regions.

Analysis of a larger number of mice analysed by PCR identified 7 mice which carried both targeting events (FIG. 13). Breeding of these mice with Cre expressers showed locus deletion, resulting in production of a mouse with deletion of the IgH C gene cluster on one allele.

Example 8

PCR Screening for IgH C Knock Out (Deletion) Mice

Primers

| NAME SEQUENCE (5' to 3') | NAME (J. Coadwell) | LENGTH (L. Ren) |
|---|---|---|
| P1 V00818f.pri AGAGCCCCCTGTCTGATAAGAATCTGG | MIgHKO1F | 27 bp |

P1 corresponds to SEQ ID NO: 5, this is a forward primer that binds to the μ region.

| NAME | NAME | LENGTH |
|---|---|---|
| P2 Puromycinr.pri TGGATGTGGAATGTGTGCGAGGC | MIgHKO2R | 23 bp |

P2 corresponds to SEQ ID NO: 6, this is a reverse primer that binds to the μ region.

| NAME | NAME | LENGTH |
|---|---|---|
| P3 Neomycinf.pri TGCTTTACGGTATCGCCGCTCCC | MIgHKO3F | 23 bp |

P3 corresponds to SEQ ID NO: 7, this is a forward primer that binds to the 3' enhancer region.

| NAME | NAME | LENGTH |
|---|---|---|
| P4 X96607r.pri GAGTCCCCATCCCCAAGGCTGG | MIgHKO4R | 22 bp |

P4 corresponds to SEQ ID NO: 8, this is a reverse primer that binds to the 3' enhancer region.

PCR Methods

For each of the PCRs used for the mouse IgH knock-out screening the reactions were set up as follows:
Per 20 μl reaction;

| 10 × buffer | 2.0 μl |
|---|---|
|  | 31/53 |
| 2 mM dNTPs | 2.0 μl |
| 20 mM forward primer | 0.8 μl |
| 20 mM reverse primer | 0.8 μl |
| lab-prep. Taq | 0.1 μl |
| diluted tail DNA | 1.0 μl |
| water | 13.3 μl |

The forward and reverse primer pairs used for each PCR type were:

| i. and | 212 PCR | MIgHKO1F | (SEQ ID NO: 5) |
|---|---|---|---|
|  |  | MIgHKO2R | (SEQ ID NO: 6) |
| ii. and | 355 PCR | MIgHKO3F | (SEQ ID NO: 7) |
|  |  | MIgHKO4R | (SEQ ID NO: 8) |
| iii. and | deletion PCR | MIgHKO1F | (SEQ ID NO: 5) |
|  |  | MIgHKO4R | (SEQ ID NO: 8) |

The 10× buffer used was:
500 mM KCl
0.05% Tween20
100 mM Tris-Cl pH 9.0
1.5 mM $MgCl_2$.

The reactions were performed as follows:
5 minutes at 95° C. for 1 cycle, 30 seconds at 94° C., then 45 seconds at the appropriate annealing temperature, followed by 1 minute at 72° C. for 30 cycles, then 10 minutes at 72° C. for 1 cycle. After which the reactions were held at 6° C. until they were analysed.

The annealing temperatures used for each reaction type were:

| i. | 212 PCR | 62° C. |
|---|---|---|
| ii. | 355 PCR | 62° C. |
| iii. | deletion PCR | 66° C. |

Example 9

Allelic Mosaicism is Transmitted Throughout the Germline

Breeding results from the first 2 germline transmission mice carrying both targeting events, $\mu^{lox}$ and $3'E^{lox}$, with Cre+ animals (1st generation) and the further breeding of C-deletion (CΔ)☐ mice to obtain homozygous animals without any remaining IgH C-genes (2nd generation) are illustrated in table 1

TABLE 1

Transmission rate of homologous integration and locus deletion.

| Genotype: 1st generation[a] | | | Genotype: 2nd generation[b] | | |
|---|---|---|---|---|---|
| homologous integration | deletion | Number (%) | homologous integration | deletion | Number (%) |
| − | + | 0 (0) | − | + | 4 (11)* |
| + | + | 2 (5)* | − | + | 0 (0) |
| + | − | 24 (60) | + | − | 10 (26) |
| Wildtype | | 14 (35) | wildtype | | 24 (63) |

[a]Germline-transmission mice carrying both targeting events ($\mu^{lox}$ and 3($E^{lox}$) were crossed with heteroxzgous Cre mice. From 71 first generation mice analysed by PCT, 40 were Cre+ and for those animals the presence of targeted integration and locus deletion is shown.
[b]Deletion mice from the 1st generation (*) were further crossed with normal F1 mice which resulted in 38 animals analysed by PCR with either locus deletion or, separately, the targeting events or without any modification.

In the 1st generation mice produced, Cre transmission was somewhat better then the 50% expected with a large number of mice carrying the targeting events. This implied that both targeted integrations occurred on one allele although the size and complexity of the IgH locus did not allow determination of the chromosomal linkage by molecular means. However, in these 1st generation animals CΔ was only accomplished in two mice, which also retained the PCR bands for the targeting events (FIG. 15). Such low level of Cre-loxP-mediated deletion accompanied by locus mosaicism was not apparent in previous breedings using the Cre pBS185 mice [15]. This could be due to diminished deletion efficiency in heterozygous mice due to reduced Cre levels or alternatively inaccessibility of the IgH locus. Breeding combinations of Cre+ male or female animals with μ$^{lox}$ 3'E$^{lox}$ mice did not change this outcome. Nonetheless, the findings suggested that locus deletion could be achieved but not with a high efficiency in all cells. Working on the assumption that Cre-loxP-mediated deletion can be operative early in fetal development proved to be correct, as further breeding of mice carrying the targeted deletion and the 2 homologous integration events resulted in offspring with transmitted deletion and without any remaining targeted integration (FIG. 15, lane 4 and 5). The frequency with which heterozygous CΔ mice were obtained from mating of mosaic founders was considerably lower than transmission of the targeted integrations or indeed the number of wildtype mice, which suggests the following events. A fertilised egg carries one IgH wildtype allele, one double-targeted IgH allele and Cre randomly integrated in the genome. Cre-mediated deletion operates disproportionately, and at the 4-cell stage only one blastomere carries the deleted allele and a wildtype allele whilst the other 3 blastomeres carry each a double-targeted allele and a wildtype allele. This distribution pattern is maintained in development and upon meiosis 4 of 8 germ cells (50%) have the wildtype allele, 3 of 8 (37.5%) the targeted allele and 1 of 8 (12.5%) the deletion. Although the numbers in table 1 are too small to precisely match this calculation they show that the majority of 2$^{nd}$ generation mice are wildtype, that an intermediate number of mice carry the targeted integrations and, at 11%, a close match is found for the number of CΔ mice which strongly supports the prediction that Cre-mediated recombination can be disproportionate at early developmental stages.

Example 10

PCR Analysis of Deletion and Rearrangement

Figure 1:
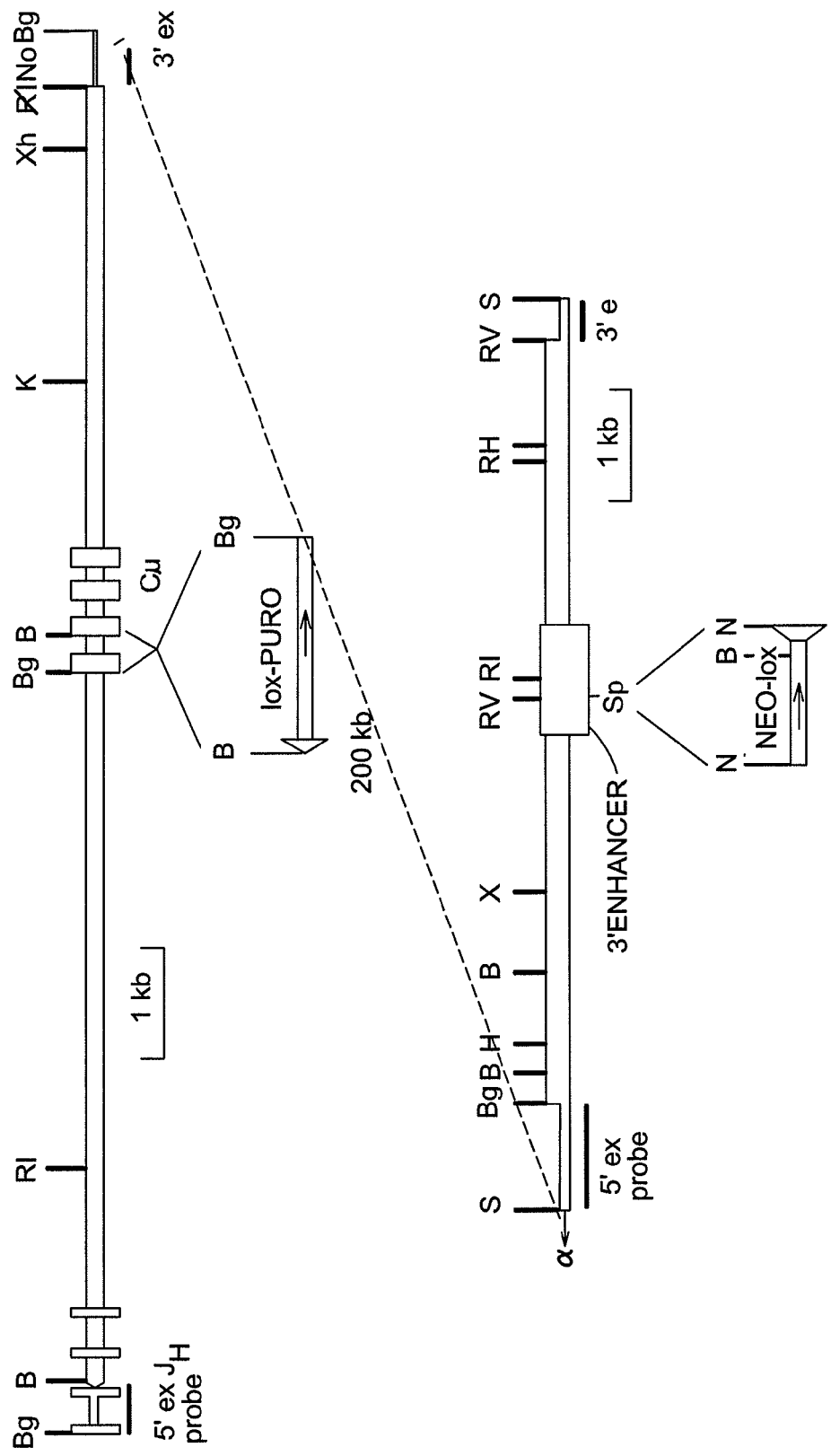
FIG. 1 illustrates the strategy for heavy chain immunoglobulin constant region gene removal. A loxP sequence upstream of a selectable marker gene (puromycin) was inserted at the most 5'C gene and another selectable marker gene (neomycin) upstream of a loxP sequence was inserted downstream of the last and most 3'Cα gene at the 3' enhancer. Upon Cre expression, this strategy resulted in the removal of a ~200 kb region with all C genes.

Homologous integration in Cμ and the α3' enhancer was identified using 2 sets of oligonucleotides (see FIG. 1): (1) Cμ forward (5'AGAGCCCCCTGTCTGATAA GAATCTGG3' SEQ ID NO: 5) and (2) puro (5'TGGATGTGGAATGTGT GCGAGGC 3' SEQ ID NO: 6), produced a ~485 bp fragment; while (3) neo (5'TGCTTTACGGTATCGCCGCTCCC 3' SEQ ID NO: 7) and (4) 3'E (5' GAGTCCCCATCCCCAAG-GCTGG 3' SEQ ID NO: 8) produced a ~500 bp fragment. Upon C gene removal oligos (1) and (4) produced a ~613 bp deletion band. The presence of the Cre-transgene and the γ2a gene in the endogenous IgH locus were identified using the following oligonucleotides: Cre for 5' GGACATGTTCAGG-GATCGCCAGG3' SEQ ID NO: 9 and Cre rev 5' GAT-AGCTGGCTGGTGGCAGATGG3' SEQ ID NO: 10, and γ2a for 5' GGCTGGGA TGGGCATAAGGATAAAGGTC3' SEQ ID NO: 11 and a 1 to 1 mixture of γ2a$^a$ rev 5'GTAGC-TATTTCTTTCCACCCAGTTCTTC3' SEQ ID NO: 12 and γ2a$^b$ rev 5' GAAAAGACTTCCTCTTTCCCAAGTGCTC3' SEQ ID NO: 13 which were allotype specific. Optimal PCR conditions were 94° C. 45 sec, 60° C. (Cre, γ2a) or 62° C. (Cμ-puro, neo-3'E) or 66° C. (Cμ-3'E) 1 min or 45 sec (Cre) and 72° C. 45 sec for 30 cycles followed by 10 min at 72° C. to complete the reaction.

For the analysis of D-J and V-D-J rearrangement, DNA and RNA was prepared from bone marrow cells using Tri Reagent (Sigma) and the One-Step RT-PCR System (Invitrogen, life technologies). Combinations of the following oligonucleotides were employed: a 1:1 mixture of DF (5' GCATGTCT-CAAAGCACAATG 3' SEQ ID NO: 14) and DQ52 (5' ACCCTGGACACAGGAAACAC 3' SEQ ID NO: 15) forward primers; a 1:1 mixture of VJ558L (5' ATGGGATG-GAGCTGGATCTT 3' SEQ ID NO: 16) and VJ558CL (5' ATGGAATGGAGCTGGGTCTT 3' SEQ ID NO: 17) forward primers; JH1-4 reverse primer (5' GAGACDGT-GASHRDRGTBCCTKSRCC 3' SEQ ID NO: 18 with R=A+G, K=G+T, H=A+T+C, B=G+T+C and D=G+A+T); and lamin B1, a ubiquitously expressed gene as control, lamin for 5' GTATGAGGCGGCACTAAACTCTAA 3' SEQ ID NO: 19, and a 1:1 mixture of lamin rev genomic 5' GAAGCCACT-GAAGAACACAAATAG 3' SEQ ID NO: 20 and lamin rev cDNA 5' TACGAAACTCCAAGTCCTCAGTAA 3' SEQ ID NO: 21. PCR conditions were 35 cycles of 92° C. 15 sec, 60° C. 30 sec and 72° C. 40 sec and RT-PCR conditions were 30 min 50° C. and 2 min 94° C. followed by 35 cycles of 92° C. 15 sec, 50° C. 30 sec and 72° C. 40 sec, followed by 10 min at 72° C. to complete the reaction.

Example 11

Block in Development at the Pre B-I Stage

To investigate the developmental capacity of the lymphocyte population in homozygous CΔ mice, bone marrow and spleen cells were analysed by flow cytometry (FIG. 16).

Flow Cytometry Analysis

Bone marrow and spleen cell suspensions were prepared from normal F1 (C57/BL6×CBA), μMT mice (μMT$^{-/-}$ (Cμ) homozygous mutant mice [11]) and CΔ deletion mice. Bone marrow cells were stained in four colour combinations (see FIG. 4) with PE-conjugated anti-mouse c-kit (CD117, 09995B, BD PharMingen, San Diego, Calif.), APC-conjugated anti-mouse CD45R (B220, 01129A, BD PharMingen), biotin-conjugated anti-mouse CD25 (01092A, BD PharMingen), FITC-conjugated monoclonal rat anti-mouse IgM (μ chain specific, 04-6811, Zymed, San Francisco, Calif.), biotin-conjugated anti-mouse CD43 (01602D, BD PharMingen), FITC-conjugated anti-mouse IgD (02214D, BD PharMingen) and/or PE-conjugated anti-mouse Igκ L-chain (559940, BD PharMingen). Spleen cells were stained with APC-conjugated anti-mouse CD45R, Biotin-conjugated anti-mouse IgM (μ-chain specific, 02082D, BD PharMingen), PE-conjugated anti-mouse Igκ and FITC-conjugated anti-mouse CD21/CD35 (CR2/CR1, 553818, BD PharMingen). Reactions with Biotin conjugated antibodies were subsequently incubated with Tri-color conjugated streptavidin (SA10006, Caltag). Cells were analyzed on a FACSVantage and CELLQuest was used for data analysis.

For cell surface staining, labeled antibodies against the pan B-cell marker B220 (CD45R) were used in combination with antibodies that allowed the identification of the various successive differentiation stages in B-cell development. In bone marrow (FIG. 16A) this showed that populations at the progenitor and precursor stage, c-kit+ B220+ pro and pre B-cells and CD43+ B220+ pre B-cells, are maintained but that more mature B220+ lymphocytes are lacking. The absence of a large proportion of B220+ B-cells is similarly pronounced in Cα and μMT mice with disrupted membrane exons [16] and is established at the pre B-II stage with the lack of CD25$^+$ B-cells which normally express a pre BCR with μ H-chain and surrogate L-chain. The removal of the C-gene cluster led to a complete disappearance of immature and mature B-cells expressing Ig H- and L-chain and staining for surface IgM, IgD, Igκ L-chain and CD21/35 positive mature B-cells (FIG. 16B) reveals their total absence.

Example 12

Transcriptional Inactivity Despite DNA Rearrangement

Preserving normal pro B-cell levels in CΔ mice suggests that early differentiation events may be maintained. To test the engagement of the IgH locus in DNA rearrangement, DNA from bone marrow cells was prepared and D-J and V-D-J rearrangement was analysed by PCR. For the region between DQ52 and $J_H$ a ~1200 bp fragment indicated the germline configuration whilst lower size amplification bands were the product of successful D-$J_H$ and $V_H$-D-$J_H$ recombination. In CΔ mice extensive DNA rearrangement was identified for the developmentally earlier D-J joins as well as for V-D-J recombination (FIG. 17A). PCR fragments of ~500 bp for D-J and >300 bp for V-D-J rearrangement were predicted, with larger bands representing amplifications from remaining distal $J_H$s still present after recombination. The CΔ mice produced bands of the expected size range which were similar in pattern and intensity to those found in normal mice and μMT mice analysed in parallel. For transcriptional analyses RNA was prepared from bone marrow cells and single-step RT-PCR using RNA from ~$10^6$ cells per reaction revealed that little or no rearranged H-chain transcripts were produced in CΔ mice (FIG. 17B). A remaining low level of transcription could be indicated by the faint bands in some of the reactions, alternatively, this may represent the background due to the low stringency of the reaction or the oligonucleotides used for amplification. However, using RNA from normal mice as well as μMT mice produced discernible RT-PCR bands of the expected size range which established a marked difference after H-chain DNA rearrangement between μMT mice exhibiting fully functional H-chain transcription and CA mice with transcriptionally silent H-chain. We repeated the PCR and RT-PCR analysis with ~$10^5$ and ~$5\times10^5$ CD43$^+$ B220$^+$ bone marrow cells, respectively, sorted by flow cytometry. Distinct bands but less diverse patterns were obtained for normal and μMT mice, but again CΔ mice did not yield any RT-PCR products (data not shown). PCR amplification of lamin B1, a ubiquitously expressed gene used as a control, produced a genomic fragment of ~433 bp and a cDNA product of ~215 bp, identified in all mice.

The finding that CΔ mice are transcriptionally inactive agrees with their lack of serum antibodies.

ELISA

Serum antibodies were captured by ELISA [33] on Falcon plates (353911, Becton Dickinson) coated with 50 μl of 10 μg/ml anti-IgM (μ-chain specific) (Sigma M-8644), anti-IgG (γ-chain specific) (Binding Site AU272), anti-IgA (α-chain specific) (Sigma M-8769) or anti-mouse κL-chain (Sigma K-2132). Bound antibody was identified using biotinylated anti-Ig (1/500 dilution, Amersham RPN 1001) or anti-κ (1/200 dilution, Zymed 04-6640) followed by a 1/200 dilution of streptavidin-conjugated horseradish peroxidase (Amersham 1052). $A_{492}$ was measured in a Titertek Multiskan MCC/340.

In ELISA no presence of any Ig or individual fractions of IgM, IgG or IgA were found in the serum of CΔ mice (FIG. 18) whilst Ig expression in μMT mice appeared to be similar to previously reported expression levels [12-14]. The defect in Ig production, re-emphasised by the lack of Igκ shows that no antibody H-chain fragments or L-chains on their own are being expressed in CΔ mice.

Targeted insertion of loxP sites, 5' and 3' of the $C_H$-gene cluster, allowed Cre-mediated removal of a ~200 kb region which produced an Ig deficient mouse line. While in vitro deletion was accomplished with the expected efficiency by transient Cre expression, in vivo C-gene removal by breeding with ubiquitous Cre expressers proved difficult. As a result, and despite normal transmission of the Cre-transgene, few animals carried the C-gene deletion (see Table 1). Such a lack of efficiency was not observed when ~400 kb of the Igλ L-chain locus were removed by breeding with the Cre mouse line [15,17 and ENSEMBL Mouse Release 17.30.1 (NCBI 30 assembly)] and it is unclear why different levels of efficiency operate on the two targeted Ig loci. In the first generation of mice carrying the C-gene deletion (litters from Cre$^+$ mice mated with μ$^{lox}$ 3'E$^{lox}$ mice), analysed by PCR of tail DNA, the deletion band was always accompanied by the presence of bands for the targeting events. A problem with the efficiency of Cre-mediated recombination has been linked to its promoter and it has been shown that the major immediate early promoter from human cytomegalovirus (CMV), used in our Cre mice, is less efficient that the equivalent murine CMV promoter [18]. Both ubiquitous and conditional expression of the Cre-gene, showed a variation in efficiency [19,20] and this may explain why Cre-mediated deletion of the C-gene locus was only achieved successfully in a varied proportion of cells and tissues producing a mosaic pattern. Nevertheless, C-gene deletion can be accomplished early on to secure modified germ cell development which allowed homozygous mice without remaining C-genes to be established by breeding.

The experiments show that removal of all C-genes silences the IgH locus at the transcriptional level, but not at the DNA rearrangement stage. This implies that locus activation is fully maintained and indeed the levels of early B-cells at the pro to pre B-cell differentiation stage, c-kit$^+$ B220$^+$ and CD43$^+$ B220$^+$, are comparable to those in normal mice. Nonetheless, with the lack of CD25$^+$ B220$^+$ cells (see FIG. 16), a complete block in development is accomplished at the pre B-II stage when rearranged Ig H-chains should be transcribed and expressed. Staining B-cell populations from bone marrow and spleen with antibodies specific for differentiation markers revealed a very similar developmental pattern for μMT and CΔ mice which is also confirmed at the DNA level where both strains show extensive rearrangement (ref. 14 and FIG. 17). However, regarding Ig expression there are fundamental differences between the CΔ and μMT strains which are not apparent using flow cytometry analysis of B-cell development where small populations of mature B-cells can escape detection. That these mature B cells are present in the bone marrow of μMT mice, but not in CΔ mice, became clear in RT-PCR reactions. Here CΔ mice appear not to produce IgH transcripts, which are abundantly present in bone marrow cells from μMT mice. To rule out any artefacts, cDNA for the identification of Ig transcripts was produced with internal $J_H$ primers. This prevented selective amplification of polyadenylated RNA, an unlikely H-chain product in CΔ mice lacking the 3' untranslated region essential for mRNA processing and expression. Ig expression could be identified in the serum of μMT mice, but not in CΔ mice, which showed a complete lack of Ig in ELISA. This established that with the removal of all C-genes the IgH locus becomes fully inoperative at the transcriptional level after DNA rearrangement is completed. Unexpectedly we identified a significant amount of IgG in the serum of the μMT animals at levels that have not been seen in μMT mice of C57BL/6 background [14]. A reason could be that the μMT mice maintained as a breeding colony for a long time have lost the true C57BL/6 background, and thus permit IgG expression [12,13]. However, the intermediate IgA levels of the μMT mice are quite similar to the levels reported for μMT in the C57BL/6 background and analysis of individual mice showed that wildtype levels as in μMT of BALB/c background [12,13] could not be reached (data not shown).

In respect of other H-chain silencing approaches the removal of clusters of gene segments, such as all Vs, Ds, Js or C-genes, appears to guarantee locus insufficiency. This has been shown in $J_H$ deletion mice where a block in B-cell development has also been reported at the $CD43^+$ precursor stage [9,21], and a lack of μ transcripts from the allele carrying the deletion was found [10]. A dysfunctional H-chain locus silences L-chain expression and although the Igκ locus can rearrange at the same time or even earlier than the IgH locus, a productively rearranged L-chain is only expressed upon H-chain production ([22] and [9] and refs therein). In $J_H$ deletion mice Cκ rearrangement in $B220^+$ $CD43^+$ sorted cell populations was quite similar to wild type levels, whilst only a low level of germline transcripts could be detected in Northern blot analysis [9]. On the contrary the removal of Cμ, the first C-gene expressed and regarded essential to drive B-cell development, did not produce H-chain silent mice [1]. A likely reason for this is that the function of one C-gene can be replaced by another. In Cμ deletion mice this was accomplished by Cδ and in Cγ2a replacement, a perhaps less important C-gene further downstream, other Cγs assumed responsibility [4]. Similarly, the removal of Cδ was well tolerated and perhaps compensated by increased Igμ expression [2]. The assumption that B-cell maturation after DNA rearrangement may be critically dependent on the expression of Igμ came from transgenic mouse models, where in the initial approaches Cμ was the only C-gene on an introduced IgH locus in germline configuration ([23] and refs therein). However, this does not imply that other C-genes, e.g. Cγ, could not initiate similar developmental processes, which may be unravelled when mice with Cμ and Cδ deletion are being produced. Suggestions that perhaps a more primitive or ancient evolutionary immune system can be operative comes from the observation that IgA is expressed in silenced μMT mice [14] and that H-chain only antibodies in Camelidae do appear to bypass the Igμ precursor cell stage [24,25]. This can be tested in the CΔ mice by Cre-loxP mediated targeted gene insertion.

REFERENCES

[1] C. Lutz, et al., IgD can largely substitute for loss of IgM function in B cells, Nature 393 (1998) 797-801.

[2] L. Nitschke, M. H. Kosco, G. Kohler, M. C. Lamers, Immunoglobulin D-deficient mice can mount normal immune responses to thymus-independent and -dependent antigens, Proc. Natl. Acad. Sci. USA 90 (1993) 1887-1891.

[3] G. Achatz, L. Nitschke, M. C. Lamers, Effect of transmembrane and cytoplasmic domains of IgE on the IgE response, Science 276 (1997) 409-411.

[4] G. Pluschke et al., Generation of chimeric monoclonal antibodies from mice that carry human immunoglobulin Cγ1 heavy of Cκ light chain gene segments, Immunol. Methods 215 (1998) 27-37.

[5] Y. R. Zou, W. Müller, H. Gu, K. Rajewsky, Cre-loxP-mediated gene replacement: a mouse strain producing humanized antibodies, Current Biology 4 (1994) 1099-1103.

[6] M. Serwe, F. Sablitzky, V(D)J recombination in B cells is impaired but not blocked by targeted deletion of the immunoglobulin heavy chain intron enhancer, EMBO J. 12 (1993) 2321-2227.

[7] J. Chen, F. Young, A. Bottaro, V. Stewart, R. K. Smith, F. W. Alt, Mutations of the intronic IgH enhancer and its flanking sequences differentially affect accessibility of the J H locus, EMBO J. 12 (1993) 4635-4645.

[8] M. Cogne et al., A class switch control region at the 3' end of the immunoglobulin heavy chain locus, Cell 77 (1994) 737-747.

[9] J. Chen et al., Immunoglobulin gene rearrangement in B cell deficient mice generated by targeted deletion of the $J_H$ locus, Int. Immunol. 5 (1993) 647-656.

[10] H. Gu, Y. R. Zou, K. Rajewsky, Independent control of immunoglobulin switch recombination at individual switch regions evidenced through Cre-loxP-mediated gene targeting, Cell 73 (1993) 1155-1164.

[11] D. Kitamura, J. Roes, R. Kuhn, K. Rajewsky, A B cell-deficient mouse by targeted disruption of the membrane exon of the immunoglobulin μ chain gene, Nature 350 (1991) 423-426.

[12] Z. Orinska et al., Novel B cell population producing functional IgG in the absence of membrane IgM expression, Eur. J. Immunol. 32 (2002) 3472-3480.

[13] M. Hasan, B. Polic, M. Bralic, S. Jonjic, K. Rajewsky, Incomplete block of B cell development and immunoglobulin production in mice carrying the μMT mutation on the BALB/c background, Eur. J. Immunol. 32 (2002) 3463-3471.

[14] A. J. Macpherson et al., IgA production without μ or δ chain expression in developing B cells, Nat. Immunol. 2 (2001) 625-631.

[15] X. Zou, T. A. Piper, J. A. Smith, N. D. Allen, J. Xian, M. Brüggemann, Block in development at the pre-B-II to immature B cell stage in mice without Igκ and Igλ light chain, J. Immunol. 170 (2003) 1354-1361.

[16] T. Nikolic, G. M. Dingjan, P. J. Leenen, R. W. Hendriks, A subfraction of $B220^+$ cells in murine bone marrow and spleen does not belong to the B cell lineage but has dendritic cell characteristics. Eur. J. Immunol. 32 (2002) 686-692.

[17] M. Clamp et al., Ensembl 2002: accommodating comparative genomics, Nucleic Acids Res. 31 (2003) 38-42.

[18] C. E. Appleby et al., A novel combination of promoter and enhancers increases transgene expression in vascular smooth muscle cells in vitro and coronary arteries in vivo after adenovirus-mediated gene transfer, Gene Ther. 10 (2003) 1616-1622.

[19] K. Sakai et al., Stage- and tissue-specific expression of a Col2a1-Cre fusion gene in transgenic mice, Matrix Biol. 19 (2001) 761-767.

[20] H. Guo et al., Specificity and efficiency of Cre-mediated recombination in Emxl-Cre knock-in mice, Biochem. Biophys. Res. Commun 273 (2000) 661-665.

[21] A. Jakobovits et al., Analysis of homozygous mutant chimeric mice: deletion of the immunoglobulin heavy-chain joining region blocks B-cell development and antibody production. Proc. Natl. Acad. Sci. USA 90 (1993) 2551-2555.

[22] T. I. Novobrantseva, V. M. Martin, R. Pelanda, W. Müller, K. Rajewsky, A. Ehlich, Rearrangement and expression of immunoglobulin light chain genes can precede heavy chain expression during normal B cell development in mice, J. Exp. Med. 189 (1999) 75-88.

[23] M. Brüggemann, Human monoclonal antibodies from translocus mice. in *Molecular Biology of B-cells*. (2004) F. W. Alt, T. Honjo, M. S. Neuberger (Eds.), pp 547-561.

[24] V. K. Nguyen, A. Desmyter, S. Muyldermans, Functional Heavy-chain Antibodies in Camelidae, Adv. Immunol. 79 (2001) 261-296.

[25] V. K. Nguyen, X. Zou, M. Lauwereyes, L. Brys, M. Brüggemann, S. Muyldermans, Heavy-chain only antibodies derived from dromedary are secreted and displayed by mouse B-cells, Immunology 109 (2003) 93-101.

[26] B. Sauer, N. Henderson, Targeted insertion of exogenous DNA into the eukaryotic genome by the Cre recombinase, New Biol. 2 (1990) 441-449.

[27] X. Zou, C. Ayling, J. Xian, T. A. Piper, P. J. Barker, M. Brüggemann, Truncation of the μ heavy chain alters BCR signalling and allows recruitment of CD5+ B cells, Int. Immunol. 13 (2001) 1489-1499.

[28] S. Pettersson, G. P. Cook, M. Brüggemann, G. T. Williams, M. S. Neuberger, A second B cell-specific enhancer 3' of the immunoglobulin heavy-chain locus, Nature 344 (1990) 165-168.

[29] K. L. Tucker et al., Germ-line passage is required for establishment of methylation and expression patterns of imprinted but not of nonimprinted genes, Genes Dev. 10 (1996) 1008-1020.

[30] X. Zou, J. Xian, A. V. Popov, I. R. Rosewell, M. Müller, M. Brüggemann. Subtle differences in antibody responses and hypermutation of λ light chains in mice with a disrupted κ constant region, Eur. J. Immunol. 25 (1995) 2154-2162.

[31] J. Sambrook, E. F. Fritsch, T. Maniatis, Molecular Cloning, A laboratory Manual (1989) Cold Spring Harbor Laboratory Press.

[32] B. Hogan, R. Beddington, F. Costantini, E. Lacy, Manipulating the mouse embryo, A Laboratory Manual (1994) Cold Spring Harbor Laboratory Press.

[33] A. V. Popov, X. Zou, J. Xian, I. C. Nicholson, M. Brüggemann, A human immunoglobulin λ locus is similarly well expressed in mice and humans. J. Exp. Med. 189 (1999) 1611-1619.

---

The invention claimed is:

1. A genetically modified mouse or mouse cell characterised in that it does not comprise a nucleic acid sequence which itself encodes any endogenous immunoglobulin heavy chain constant region locus polypeptide and in that one or more endogenous Ig H Variable region, one or more endogenous Ig H D segment, and one or more endogenous Ig H J segment nucleic acid sequences are present.

2. A genetically modified mouse or mouse cell according to claim 1 characterised in that all the endogenous Ig H Variable region, D and J segment nucleic acid sequences are present.

3. A genetically modified mouse or mouse cell according to claim 1 characterised in that it does not comprise a nucleic acid sequence which itself encodes any immunoglobulin heavy chain constant region (IgH C) polypeptide.

4. A genetically modified mouse or mouse cell according to claim 1 characterised in that all immunoglobulin heavy chain constant region gene sequences are absent or partially absent from the genome.

5. A genetically modified mouse or mouse cell according to claim 1 characterised in that it is obtainable or obtained by targeted deletion of essentially all endogenous IgH C gene sequences.

6. A genetically modified mouse or mouse cell according to claim 1 characterised in that it is obtainable or obtained by Cre loxP recombination.

7. A genetically modified mouse or mouse cell according to claim 1 characterised in that at least part of at least one IgH C gene enhancer sequence is present.

8. A genetically modified mouse or mouse cell according to claim 1 characterised in that a non-endogenous site-specific recombination sequence is present within the genome.

9. A genetically modified mouse or mouse cell according to claim 1 characterised in that all eight endogenous IgH C genes $\mu$, $\delta$, $\gamma3$, $\gamma1$, $\gamma2a$, $\gamma2b$, $\epsilon$ and $\alpha$ are absent or partially absent.

10. A genetically modified mouse cell according to claim 1 characterised in that it is an embryonic stem cell.

11. A genetically modified mouse or mouse cell derived from a genetically modified mouse or mouse cell of claim 1.

* * * * *